(12) United States Patent
Bao et al.

(10) Patent No.: US 6,609,086 B1
(45) Date of Patent: Aug. 19, 2003

(54) PROFILE REFINEMENT FOR INTEGRATED CIRCUIT METROLOGY

(75) Inventors: Junwei Bao, Fremont, CA (US); Srinivas Doddi, Fremont, CA (US); Nickhil Jakatdar, Los Altos, CA (US); Vi Vuong, Fremont, CA (US)

(73) Assignee: Timbre Technologies, Inc., Santa Clara, CA (US)

( * ) Notice: Subject to any disclaimer, the term of this patent is extended or adjusted under 35 U.S.C. 154(b) by 40 days.

(21) Appl. No.: 10/075,904

(22) Filed: Feb. 12, 2002

(51) Int. Cl.[7] .................. G06F 19/00; G01B 11/04; G01B 11/08
(52) U.S. Cl. ................ 702/189; 356/636; 702/155
(58) Field of Search ................ 702/189, 155, 702/159, 166, 172; 356/629, 634, 635, 636, 638, 639, 640, 902

(56) References Cited

U.S. PATENT DOCUMENTS

| | | | |
|---|---|---|---|
| 6,429,943 B1 * | 8/2002 | Opsal et al. | 356/625 |
| 2002/0033945 A1 * | 3/2002 | Xu et al. | 356/369 |
| 2002/0038196 A1 * | 3/2002 | Johnson et al. | 702/179 |
| 2002/0090744 A1 * | 7/2002 | Brill et al. | 438/11 |
| 2002/0149782 A1 * | 10/2002 | Raymond | 356/616 |
| 2002/0158193 A1 * | 10/2002 | Sezginer et al. | 250/237 G |
| 2003/0028358 A1 * | 2/2003 | Niu et al. | 703/2 |
| 2003/0058443 A1 * | 3/2003 | Xu et al. | 356/369 |
| 2003/0076511 A1 * | 4/2003 | Aikens et al. | 356/636 |

OTHER PUBLICATIONS

Niu et al. "Specular Spectroscopic Scatterometry", IEEE, May. 2001.*

* cited by examiner

*Primary Examiner*—Patrick Assouad
(74) *Attorney, Agent, or Firm*—Morrison & Foerster LLP

(57) ABSTRACT

The present invention includes a method and system for determining the profile of a structure in an integrated circuit from a measured signal, the signal measured off the structure with a metrology device, selecting a best match of the measured signal in a profile data space, the profile data space having data points with a specified extent of non-linearity, and performing a refinement procedure to determine refined profile parameters. One embodiment includes a refinement procedure comprising finding a polyhedron in a function domain of cost functions of the profile library signals and profile parameters and minimizing the total cost function using the weighted average method. Other embodiments include profile parameter refinement procedures using sensitivity analysis, a clustering approach, regression-based methods, localized fine-resolution refinement library method, iterative library refinement method, and other cost optimization or refinement algorithms, procedures, and methods. Refinement of profile parameters may be invoked automatically or invoked based on predetermined criteria such as exceeding an error metric between the measured signal versus the best match profile library.

76 Claims, 16 Drawing Sheets

PROFILE REFINEMENT FOR INTEGRATED CIRCUIT METROLOGY

CROSS-REFERENCE TO RELATED APPLICATIONS

This application relates to co-pending U.S. patent application Ser. No. 09/727530, entitled "System and Method for Real-Time Library Generation of Grating Profiles" by Jakatdar, et al., filed on Nov. 28, 2000; to co-pending U.S. patent application Ser. No. 09/764,780 entitled "Caching of Intra-Layer Calculations for Rapid Rigorous Coupled-Wave Analyses" by Niu, et al., filed on Jan. 25, 2001; to co-pending U.S. patent application Ser. No. 09/737,705 entitled "System and Method for Grating Profile Classification" by Doddi, et al., filed on Dec. 14, 2000; and to co-pending U.S. patent application Ser. No. 09/923,578, entitled "Method and System of Dynamic Learning Through a Regression-Based Library Generation Process", filed Aug. 6, 2001, all owned by the assignee of this application and incorporated herein by reference.

BACKGROUND OF INVENTION

1. Field of Invention

The invention relates to integrated circuit (IC) metrology and more particularly to the use of metrology systems and profile libraries or profile data spaces to determine the critical dimensions (CD's) and profiles of IC structures.

2. Related Art

With the current drive towards smaller geometries of IC features, features measurement is increasingly difficult as the size of the features become smaller. However, knowledge of the dimensions of gratings or periodic structures is essential in order to determine if the dimensions of the features are within the acceptable ranges and if a particular fabrication process causes the sidewalls of the features to be tapered, vertical, T-topped, undercut, or have footings.

Traditionally, a sample was cleaved and examined with a scanning electron microscope (SEM) or similar device. The cross-section SEM method is typically slow, expensive, and destructive whereas the CD SEM method only provides one measurement number seen from the top of the feature. Spectroscopic reflectometry and ellipsometry are used to beam light on the structure and measure the spectrum of reflected signals. Current practices basically use an empirical approach where the spectra of reflected light is measured for a known width of features in a structure. This process is time consuming and expensive even for a limited library of profiles of structure dimensions and the associated spectrum data of reflected/diffracted light. Furthermore, if such a library were built for a wide range of profiles at a fine resolution, the process of building the library is time consuming and cost-prohibitive. With IC features becoming smaller, there is a need for a library with even finer resolution. As the resolution of the library increases, the size of the library increases while the time to create the library increases exponentially. Furthermore, an extensive library of profiles and spectra is inefficient for searching purposes, especially for real-time work. Thus, there is a need for a method, system, and/or apparatus that facilitates the use of metrology devices and systems for measuring profiles without creating huge profile libraries or data collections and incurring extensive searches of said profile libraries or data collections.

SUMMARY OF INVENTION

The present invention includes a method and system for determining the profile of an integrated circuit structure from a measured signal by selecting one or more best matches of the measured signal in a profile data space and performing a refinement procedure to determine refined profile parameters. The measured signal may be generated by an optical, electric, electron, or mechanical metrology device. The profile data space may be a profile library of profile parameters and corresponding signals or a collection of data points representing profile parameters and corresponding signals.

An exemplary embodiment includes a method and system for ensuring that a specified extent of non-linearity between data points exists so as to ensure consistent results from the refinement calculations.

Another exemplary embodiment includes a refinement procedure comprising finding a polyhedron in the data space of profile parameters, the polyhedron configured to contain the profile parameters of the best match library spectrum and also configured such that the corners of the polyhedron correspond to selected profile parameter data point, one for each profile parameter. The total cost function of the best match spectrum and spectra of the selected data points compared to the measured spectrum is minimized utilizing a weighting factor. An alternative approach is finding a polyhedron configured to contain the profile parameters of the best match library spectrum and also configured such that the corners of the polyhedron correspond to selected profile parameter data point, two for each profile parameter. Still another embodiment includes calculation of the refined profile parameters by using a sensitivity matrix to determine profile parameter adjustment values.

Alternatively, a clustering approach is used to select cluster representatives for each cluster of profile library instances and to derive an adjustment multiplier for each profile parameter value of the cluster representative. The refined profile parameters are calculated by multiplying the measured diffracted spectrum by the corresponding adjustment multiplier for each profile parameter value of the best matching cluster representative. In another application, the adjustment multiplier is derived from selected profile library instances according to selection criteria.

Yet another embodiment is a regression-based refinement method wherein data points within a data space of signals and profile parameters are successively evaluated for goodness of fit compared to the measured spectrum. Subsequent regression data points are selected using global and local optimization techniques. The signals for subsequent regression data points are calculated using metrology simulation procedures.

Furthermore, the present invention may utilize localized fine-resolution refinement library methods, iterative library refinement methods, other cost optimization methods, and/or other refinement algorithms or techniques. The refinement procedure may be invoked automatically or invoked based on occurrence of predetermined criteria such as exceeding an error metric between the measured signal versus the best match profile library signal.

DETAILED DESCRIPTION OF EXEMPLARY EMBODIMENT(S)

In order to facilitate the description of the present invention, an optical metrology system is used to illustrate the concepts and principles. It is understood that the same concepts and principles equally apply to the other IC metrology systems as will be discussed below. In a similar manner, although a profile library is frequently used to illustrate concepts and principles, the present invention equally applies to a data space comprising profile parameters and corresponding metrology signals.

Figure 1:
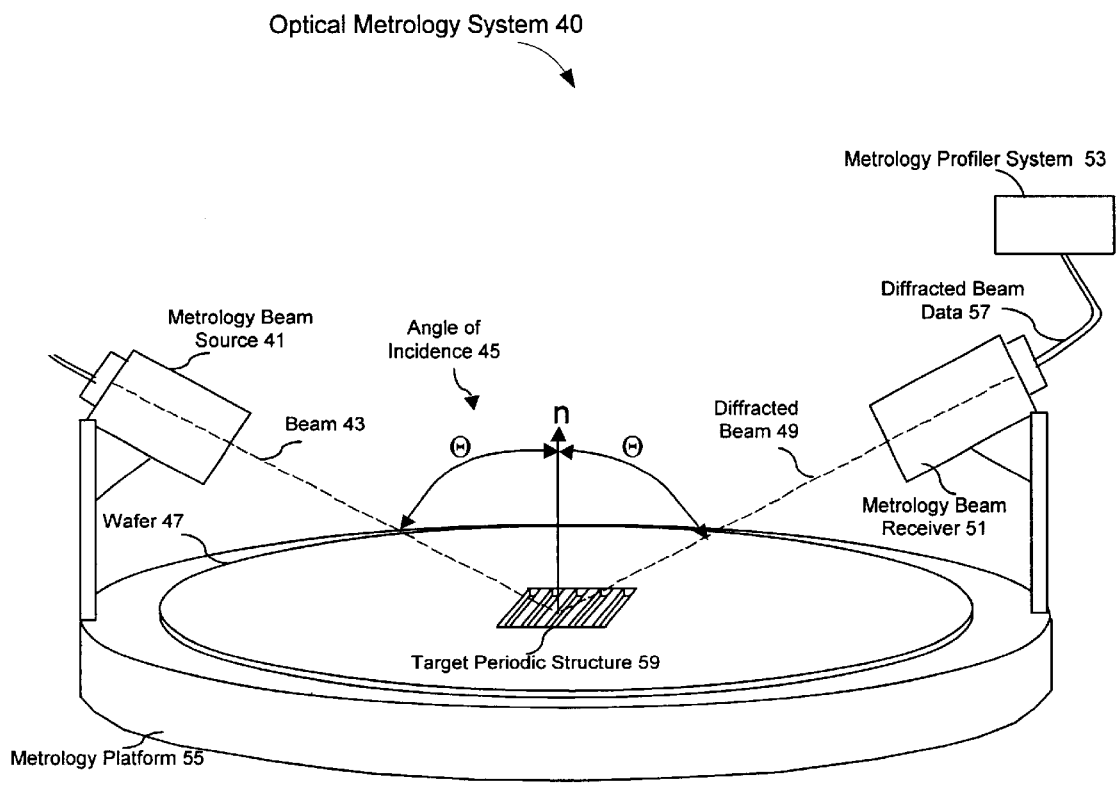
FIG. 1 is an architectural diagram illustrating the use of optical metrology to measure the diffracted spectra off integrated circuit periodic structures.

FIG. 1 is an architectural diagram illustrating the use of optical metrology to measure the diffracted spectra off integrated circuit periodic structures. The optical metrology system 40 consists of a metrology beam source 41 projecting a beam 43 at the target periodic structure 59 of a wafer 47 mounted on a metrology platform 55. The metrology beam 43 is projected at an incidence angle θ towards the target periodic structure 59. The diffracted beam 49 is measured by a metrology beam receiver 51. The diffracted beam data 57 is transmitted to a metrology profiler system 53. The metrology profiler system 53 compares the measured diffracted beam data 57 against a library of calculated diffracted beam data representing varying combinations of profile parameters of the target periodic structure and resolution. The library instance best matching the measured diffracted beam data 57 is selected. The profile and associated critical dimensions of the selected library instance correspond to the cross-sectional profile and critical dimensions of the features of the target periodic structure 59. The optical metrology system 40 may utilize a reflectometer, an ellipsometer, or other optical metrology device to measure the diffracted beam or spectrum. An optical metrology system is described in co-pending U.S. patent application Ser. No. 09/727,530 entitled "System and Method for Real-Time Library Generation of Grating Profiles" by Jakatdar, et al., filed on Nov. 28, 2000, and is incorporated in its entirety herein by reference.

Figure 2A:
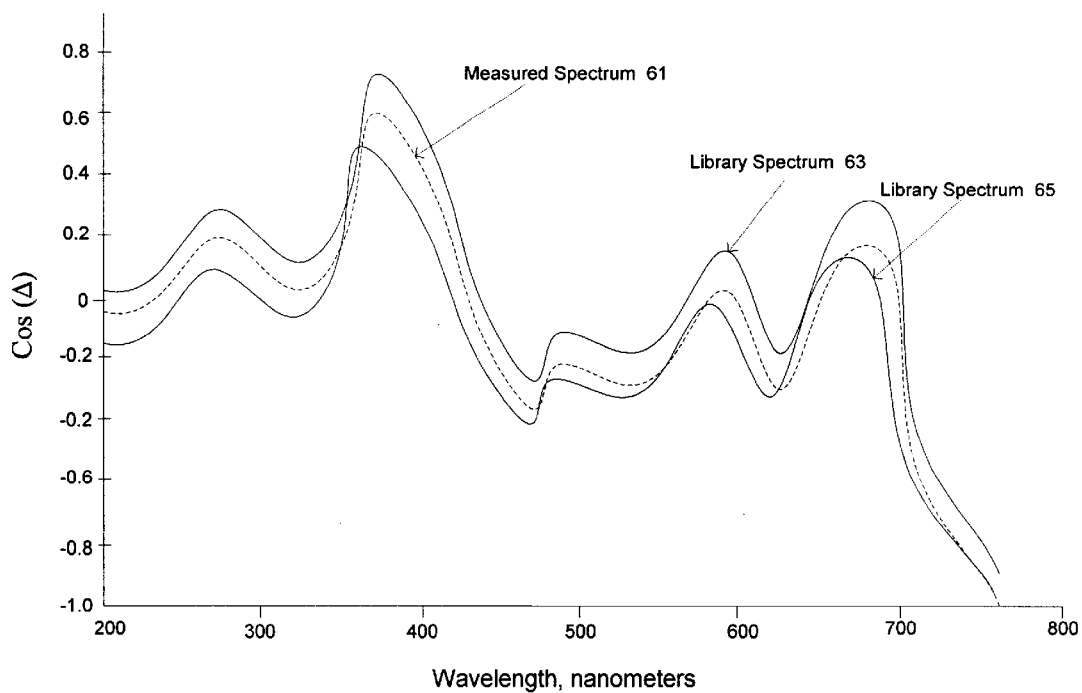
FIG. 2A illustrates a measured diffracted spectrum graph compared to diffracted spectra graphs of instances in a profile library.

FIG. 2A illustrates a measured diffracted spectrum graph compared to diffracted spectra graphs of instances in a profile library. The wavelength in nanometers (nm) is shown in the X-axis and cosine ($\Delta$), an ellipsometric measurement of the diffracted spectrum, in the Y-axis. A profile library is created with ranges of CD's and other profile parameters of structures in a wafer. The number of instances of the profile library is a function, of the combinations of the various CD's and other profile parameters, at the specified resolution. For example, the range of the top CD for a structure may be from 100 to 300 nm and the specified resolution is 10 nm. In combination with the other profile parameters of the structure, one or more instances of the profile library are created starting at 100 nm top CD and for every, 10 nm increment thereafter until 300 nm. For a detailed description of parameters used to create a profile library, refer to co-pending U.S. patent application Ser. No. 09/727,530 entitled "System and Method for Real-Time Library Generation of Grating Profiles" by Jakatdar, et al., filed on Nov. 28, 2000, which is incorporated herein by reference. For example, instances of a profile library for trapezoidal profiles may have diffracted spectra and profile parameters including a top CD, a bottom CD, and height. In FIG. 2A, library spectrum 63 representing a set of the profile parameters at a given resolution and another library spectrum 65 with a different set of profile parameters at the same resolution are illustrated. The measured spectrum 61 is in close proximity to the library spectra 63 and 65. One aspect of the present invention is to determine the profile that corresponds to the measured diffracted spectrum 61 based on the measured diffracted spectrum 61 and on known values in the profile library.

Figure 2B:
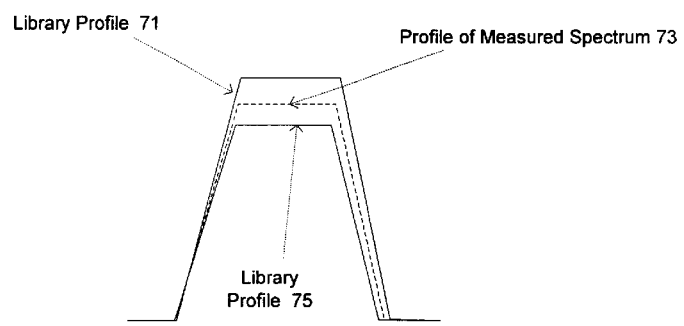
FIG. 2B illustrates a structure profile of a measured periodic structure compared to profiles of instances in a profile library.

FIG. 2B illustrates a structure profile of a measured periodic structure compared to profiles of instances in a profile library. A library profile 71 of a trapezoidal structure is illustrated with another similar library profile 75. A measured diffracted spectrum corresponds to a profile 73, shown as a dotted line, with profile parameters that are in close proximity to library profiles 71 and 75. One aspect of the present invention is to determine the profile parameters that correspond to the measured diffracted spectrum, the determination based on the measured diffracted spectrum and on data selected from the profile library or on data derived using simulation techniques. As an example, assume that library profile 71 corresponds to library spectrum 63 and that library profile 75 corresponds to library spectrum 65. As depicted in FIG. 2A, neither library spectrum 63 or 65 exactly matches the measured spectrum 61. As such, in most conventional systems, based on a "best match" algorithm, either spectrum 63 or 65 would be selected as the closest match. However, this results in a certain amount of error. For example, assume that library spectrum 65 is selected as a match for measured spectrum 61. In that case, library profile 75 is selected as representing the actual profile of the periodic grating. However, as depicted in FIG. 2B, there is a difference/error between library profile 75 and the actual profile of the periodic grating (i.e., profile of measured spectrum 73). One solution may be to increase the resolution of the library so that there would be a library spectrum that more closely matches the measured spectrum. However, this increases the size of the library, which has the disadvantage of more time and computation to generate the library, to store the library, and to search the library. As such, in the exemplary embodiments described below, a profile refinement process is utilized to determine a more closely matching spectrum/profile based on the existing library spectra/profiles and the measured spectrum.

Figure 3:
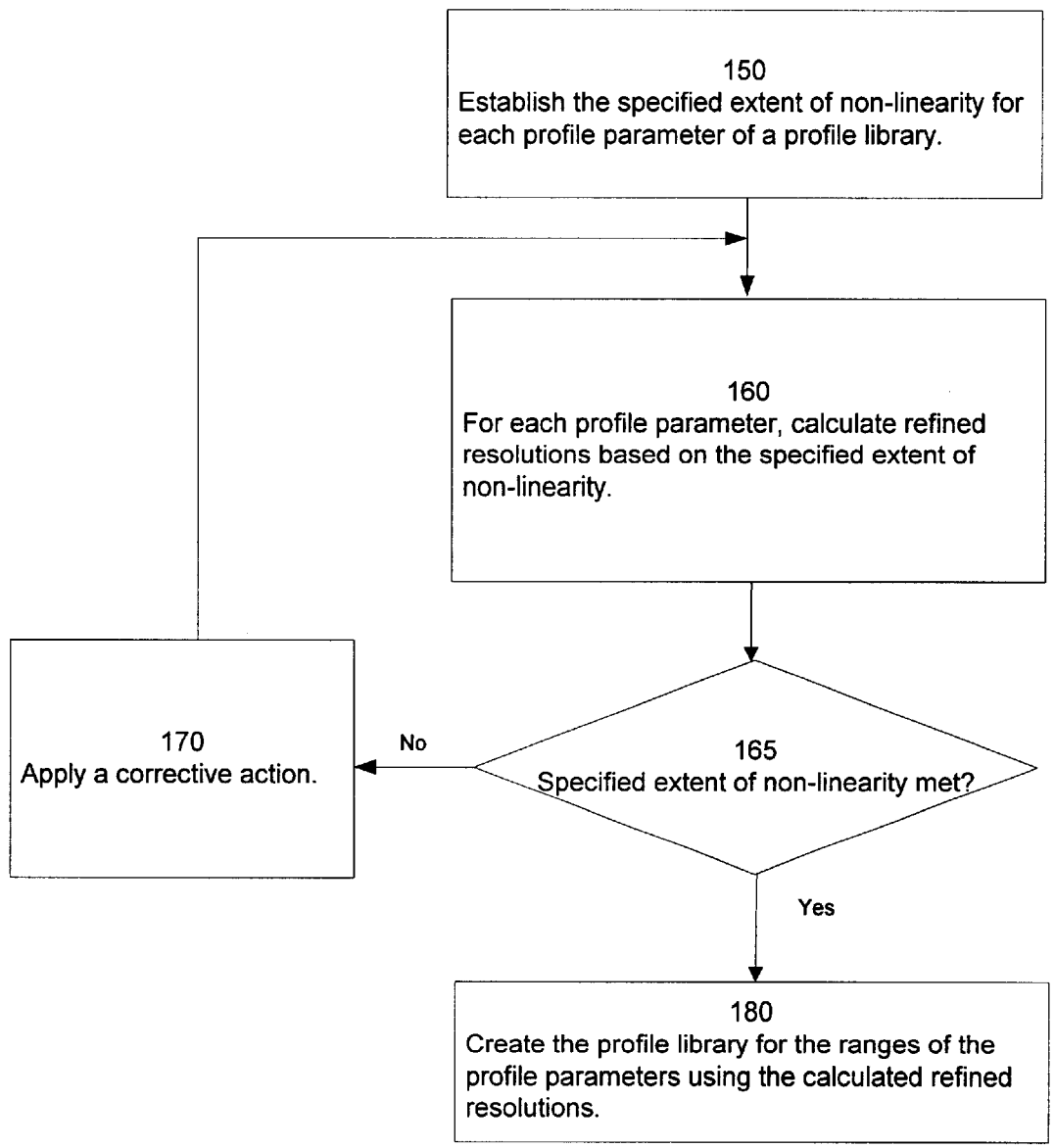
FIG. 3 is a flow chart of operational steps for creating a profile library with a specified extent of non-linearity in an exemplary embodiment of the present invention.

FIG. 3 is a flow chart of operational steps for ensuring the specified extent of non-linearity between library data points in an exemplary embodiment of the present invention. A data point is a set of profile parameters with an associated spectrum. When the sets of profile parameters and associated spectra are organized in the form of a library, the term library data point is used. It should be understood that the principles and concepts of the present invention would apply regardless of the method of organizing the data. A set of data points is a profile data space or data space in short.

The concept of linearity is conventionally illustrated with a graph of a straight line at 45 degrees on X–Y axes. Thus, when two variables X and Y have a linear relationship, for every increment of X, there is a corresponding increment of Y, and the relationship of X to Y can be represented on a graph as a straight line. In this application, instead of linearity, it is the extent of non-linearity between the data points that is controlled in order to ensure consistent and repeatable results from refinement procedures used to determine the more closely matching profile parameters and spectrum. For a given variable, the extent of non-linearity may be measured as the deviation of the calculated number versus the value of the same variable if the relationship of the variables is linear. In the present embodiment, the extent of non-linearity of the library data points is expressed as the difference of the calculated change of the profile parameters from the actual change of the profile parameters, which will be described below. The present embodiment also ensures that the specified extent of non-linearity exists by utilizing refined resolutions for each profile parameter used to create the profile library. As will also be described with examples below, refined resolutions are the maximum value of the profile parameter resolutions that can be used to create a profile library while maintaining the specified extent of non-linearity between data points. A profile library created with the specified extent of non-linearity between data points enables refinement of the profile parameters such that the calculated refined profile parameters do not exceed a certain maximum deviation or threshold deviation. For example, for a set of profile parameters consisting of CD width and height, the threshold deviations specified for a fabrication run may be 1.5 nm and 2 nm respectively for CD width and for height of the IC structure, i.e., the structure may vary by these amounts without impacting the design attributes of the structure. The present embodiment calculates the maximum resolution for the CD width and height for creating the library such that the deviation or error of calculated refined profile parameters using the created library do not exceed for example 1.5 nm and 2 nm respectively.

Referring to FIG. 3, the specified extent of non-linearity for each profile parameter of a profile library is established 150. As discussed above, one embodiment utilizes the concept of establishing a threshold deviation for each profile parameter of a profile library for specifying the desired extent of non-linearity. Threshold deviation may be the maximum deviation from a structure profile parameter specification without altering the design attributes of the device or circuit. Alternatively, threshold deviations are those set by users of the IC structures and wafers based on their requirements. For each profile parameter, the refined resolution based on the specified extent of non-linearity is calculated 160. One exemplary technique for determining the refined resolution in a case where the extent of non-linearity is expressed as threshold deviations is by using a sensitivity matrix to calculate the profile parameter change and by comparing the calculated profile parameter change to the established threshold deviation for that profile parameter. The steps below describe the procedure:

1) Given a set of profile parameters, P, for a profile library, $P=(P_1, P_2, \ldots P_K)$, establish the threshold deviation of each profile parameter, expressed as a vector:

$$\text{Threshold Deviation } T=(T_1, T_2, \ldots T_K)$$

where K is the number of profile parameter dimensions.

2) Select a set of profile parameters, $P_{SET0}$, as follows:

$$P_{SET0}=(P_1, \ldots P_{L-1}, P_L, P_{L+1}, \ldots P_K) \quad (1.00)$$

where L is any profile parameter from 1 to K.

3) Simulate the diffracted spectrum off an IC structure using the profile parameters selected, $P_{SET0}$, generating diffracted spectrum $S^0$.

4) Select one profile parameter $P_L$ of the selected set, $P_{SET0}$, and increment the selected profile parameter $P_L$ by a small amount $\beta_L$, designating the new set $P_{INCR}$. For example, $P_L$ may be the CD width and CD width may range from 100 to 300 nm while the increment $\beta_L$ may be 1 or 2 nm. However, the increment for the profile parameter may vary depending on experience from previous library creation processes for the particular fabrication run.

5) Simulate the diffracted spectrum off an IC structure with the profile parameters set $P_{INCR}$, generating diffracted spectrum $S^L$.

6) Calculate the sensitivity of change of spectrum, $\delta S$, corresponding to the change in the profile parameter, $\delta P$:

$$\frac{\delta S^L}{\delta P} = \frac{(S^L - S^0)}{\beta_L} \quad (1.20)$$

where $S^L$ is a column vector of length N, and N is the number of spectrum data points for each measurement performed with the metrology device.

7) Change one of the other profile parameters by a small increment α, for example, α 0.2 nm. The small increment a is application dependent and generally based on empirical date; while the small increment a is typically a fraction of the profile increment $\beta_L$.

8) Simulate the diffracted spectrum using the changed profile parameter while the rest of the profile parameters are held constant, generating diffracted spectrum $S^i$. Repeat this step for all the other profile parameters. For a profile parameter i, the general form of the equation is:

$$\frac{\delta S^i}{\delta P_i} = \frac{(S^i - S^0)}{\alpha} \quad (1.40)$$

where $\delta S^i$ is the change of the diffracted spectrum induced by the change in profile parameter $\delta P_i$, each of the $S^i$ is a column vector of length N, and N is the number of spectrum data points for each measurement performed with the metrology device.

9) Compute the sensitivity matrix J substituting the values calculated in foregoing steps:

$$J = \left[\frac{\delta S^1}{\delta P_1}, \frac{\delta S^2}{\delta P_2}, \ldots \delta\frac{S^K}{\delta P_K}\right] \quad (1.60)$$

where $S^1$ is a column vector of length N, $S^2$ is a column vector of length N, etc., and N is the number of spectrum data points for each measurement performed with the metrology device.

10) Simulate the diffracted spectrum using the set of profile parameters:

$$P=(P_1, \ldots P_{L-}, (P_L + \beta_L/2), P_{L+1}, \ldots P_K) \quad (1.80)$$

generating diffracted spectrum S.

11) Using the sensitivity matrix J calculated above and the new $\delta S$ value from the equation $\delta S=S-S^0$, calculate $\delta P$ as follows:

$$\delta P=(J^T J)^{-1} J^T \delta S \quad (2.00)$$

yielding $\delta P=(b_1, \ldots b_{L-1}, b_L, b_{L+1}, \ldots b_K)$
where $b_1$ is the calculated value of the change in profile parameter 1, $b_L$ is the calculated value of change in profile parameter $P_L$, and so on.

Referring to FIG. 3, the extent of non-linearity of a profile library created with the refined resolution or resolutions calculated using the above steps is tested to see if these meet the specified extent of non-linearity 165. If the linearity test requirement is not met, a corrective action is applied 170.

An example of performing the linearity test and applying a corrective action is described below for the technique using threshold deviations:

12) The calculated $\delta P$ is compared to the ideal values of $\delta P$ and the absolute values of the differences between the ideal values of $\delta P$ and calculated values of $\delta P$ are tested to see if these are equal to or less than the threshold deviations. Ideal values for the profile parameter of $\delta P$ are zero for parameters other than $P_L$ and one half of $\beta_L$ for the profile parameter $P_L$. Expressed in equation form, the linearity test is as follows:

$$\text{Compare } |0 - b_1| \leq T_1 \quad (2.10)$$
$$\vdots$$
$$|\beta_L/2 - b_L| \leq T_L$$
$$\vdots$$
$$|0 - b_K| \leq T_K$$

If the comparison in equation (2.10) is True, i.e., the maximum threshold deviation for profile parameter $P_L$ has not been exceeded, then increment the value of $\beta_L$. For example, $\beta_L$ may be incremented by 1 nm. Repeat Steps 5 through 12 until the comparison is False and take the last value of $\beta_L$ where the comparison was True, this value of $\beta_L$ being the refined profile resolution for the profile parameter $P_L$.

13) Repeat Steps 1 through 12 for the rest of the profile parameters and save the refined profile resolutions.

Referring again to FIG. 3, the profile library is created for the ranges of the profile parameters, using the calculated refined resolutions 180. For example, the CD width may have a range of 100 to 200 nm and the refined resolution of the CD width that meets the specified threshold deviations may be 4 nm.

Another embodiment for determining refined resolutions of the profile parameters recognizes that in order for the linearity requirement to be satisfied, more than one refined resolution is needed. This approach recognizes that over the entire range of the profile parameters, different resolutions may apply. The entire range of the profile parameters is thus partitioned into several partitions. Within each partition, refined profile parameter resolutions are determined in a similar manner as described above. Instead of using one set of refined resolutions to create a profile library, a set of refined resolutions specific to profile parameter partition is used. Using the previous example, the CD width may have a range of 100 to 300 nm and the refined resolution of the CD width may be 3 nm for the first partition 100–200 nm, 2.5 nm for the second partition of 201–250 nm, and 1.8 nm for the third partition 251–300 nm. It is understood that to a person knowledgeable in the art, other techniques or algorithms may be employed to perform a linearity test or ensure that the set of profile data points in a library meet linearity requirements.

FIG. 4A through FIG. 11 use optical metrology to illustrate and describe the concepts and principles used in the present invention. As mentioned above, the concepts and principles described also apply to other metrology systems such as electron, electric, and mechanical metrology systems.

Figure 4A:
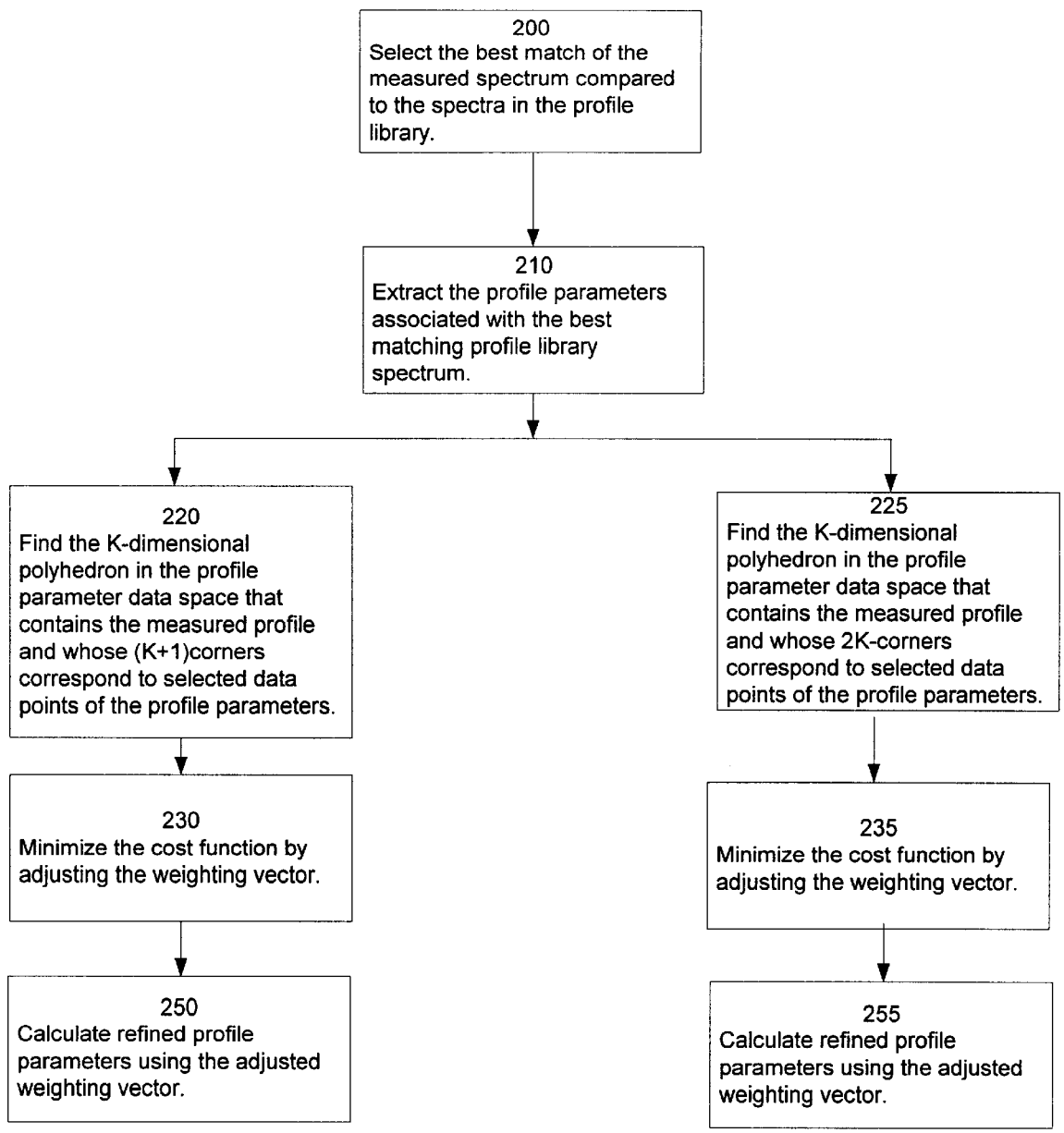
FIG. 4A is a flow chart of operational steps for profile refinement by, minimizing the cost function in exemplary embodiments of the present invention.

FIG. 4A is a flow chart of operational steps for profile refinement by minimizing the cost function of selected spectra data points in the profile library compared to the measured diffracted spectra and utilizing a weighting vector in exemplary embodiments of the present invention. The profile refinement process is performed after creating a library with a specified extent of non-linearity. The measured diffracted spectrum, $S^M$, off an IC structure is compared to the spectra in the profile library and the best match spectrum, $S^0$, in the library is selected 200. The profile parameters associated with the best match library spectrum are extracted 210. The data point representing the profile parameters associated with the best match library spectrum is designated as $P^0$.

Figure 4B:
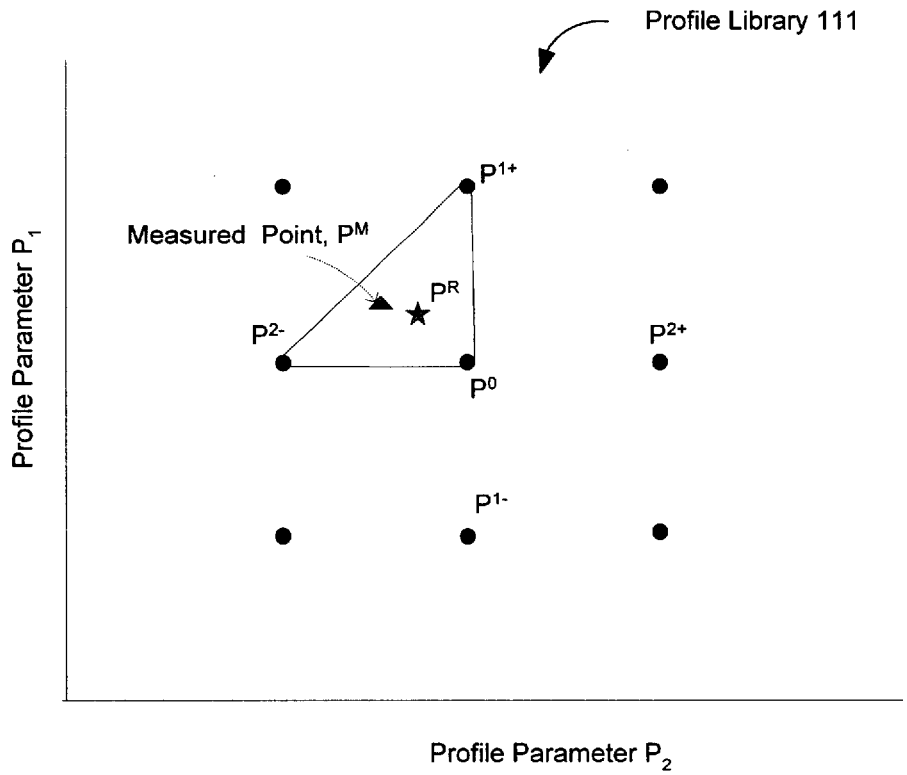
FIGS. 4B and 4C are graphical illustrations of profile refinement using cost optimization in exemplary embodiments of the present invention.

The total cost function of selected spectra data points in the profile library compared to the measured diffracted spectra is calculated. The total cost function is minimized utilizing a weighting factor. Selection of spectra data points varies according to the embodiment. In one exemplary embodiment, a K-dimensional polyhedron is selected in the data space of profile parameters, the polyhedron configured to contain the profile parameters of the best match library spectrum and also configured such that the corners or vertices of the polyhedron correspond to selected profile parameter data points 220. As previously defined, a data point refers a set of profile parameters and the associated spectrum, while a data space is a collection of data points. Selection of the profile parameter data points for the K-dimensional polyhedron is done by selecting neighboring values of the profile parameters associated with the best match library spectrum, the neighboring values chosen in a direction that yields a smaller spectrum variance between the measured spectrum and the spectrum associated with the data point, as illustrated in FIG. 4B. Referring to FIG. 4B, assume a simple profile of the IC structure being a rectangle with two profile parameters used, namely, CD width $P_1$, and height $P_2$. $P^R$ is the refined or calculated parameter data point whereas $P^M$ is the actual parameter data point corresponding to the measured spectrum $S^M$. The best match profile parameter data point, $P^0$, associated with the best match spectrum, $S^0$ (not shown), is the starting point for selecting the other profile parameter data points. In the case of profile parameter $P_1$ in the Y-axis, the neighboring values of $P^0$ are $P^{1+}$ in the positive direction and $P^{1-}$ in the negative direction of $P_1$. The associated spectra (not shown) for $P^{1+}$ and $P^{1-}$ are $S^{1+}$ and $S^{1-}$ respectively. If the cost function of $S^{1+}$ compared to the measured spectrum $S^M$ versus the cost function of $S^{1-}$ compared to the measured spectrum $S^M$ is smaller, then $P^{1+}$ is selected as the data point for the CD width $P_1$, else, $P^{1-}$ is selected. A similar analysis is made for profile parameter $P_2$ and for this example, profile parameter data point $P^{2-}$ is selected for the height $P_2$. In the present example, the polyhedron is the triangular space that includes the measured parameter data point $P^M$ with corners $P^0$, $P^{1+}$, and $P^{2-}$.

For a more complex profile requiring, for example, seven profile parameters, K is equal to 7, and the polyhedron with eight corners, (K+1), is a hexahedron. A similar set of steps is applied for selecting the neighboring data points of the profile parameters regardless of the value of K. Although a rectangular profile is frequently used in the examples, the concepts and principles of the present invention are applicable to other profiles, such as non-trapezoidal profiles with top rounding, bottom footing, T-topping, undercut, with straight, concave sidewalls, or convex sidewalls and non-trapezoidal profiles with various combinations of shapes and configuration characteristics.

Referring now to FIG. 4A, the cost function of the best match spectrum relative to the measured diffracted spectrum and the cost function of spectra associated with the selected data points relative to the measured diffracted spectrum are minimized by adjusting the weighting vector 230. The equation to minimize the cost function for the present embodiment is:

$$\underset{W}{\text{MIN}}\ C(W) \qquad (2.20)$$

$$\text{such that} \sum_{i=1}^{K} W_i = 1 \qquad (2.40)$$

and $$W_i \geq 0 \qquad (2.60)$$

and where $$C(W) = \|[S^0, S^1, \ldots S^K]_{N\ (K+1)} W_{K+1} - S^M\| \qquad (2.80)$$

where:
C is the total cost function,
K is the number of profile parameter dimensions,
N is the number of spectrum data points for each measurement performed with the metrology device,
S is the diffracted spectrum, $S^0$ is the best match spectrum, $S^1$ is the spectrum associated with the chosen value of the first profile parameter, and so on up to $S^K$, and $S^M$ is the measured spectrum, and W is the weighting vector.
The weighting vector W is given by the equation:

$$\text{Weighting Vector}, W = \begin{bmatrix} W_0 \\ W_1 \\ \vdots \\ W_K \end{bmatrix} \qquad (3.00)$$

where $W_0$ is the weight for the best match data point, $W_1$ is the weight of the first profile parameter data point, and so on. The norm value of any vector V where i may be 1, 2 or any integer and for a length M is given by the equation:

$$\|V\|_i \equiv \left( \sum_{K=1}^{M} |V_K|^i \right)^{1/i}. \qquad (3.20)$$

Optimization of the value of the weighting vector is subject to two constraints, namely, first, the sum of the weighting vectors must equal one, equation (1.20) and second, the value of the weighting vector may be equal or greater than zero, equation (1.30).

Referring now to FIG. 4A, the refined profile parameters are calculated by using the weighting vector that minimizes the total cost function of the profile parameters 250 as expressed in the equation:

$$P^R = (P^0, P^1, \ldots P^K) \begin{pmatrix} W_0 \\ W_1 \\ \ldots \\ W_K \end{pmatrix} \qquad (3.40)$$

where $P^R$ is a vector representing the refined profile parameters, $P^0$ is a vector representing the profile parameters of the best match spectrum, $P^1$ and $P^K$ are vectors representing the profile parameters of the first and $K^{th}$ corners of the polyhedron. Continuing with the example of a rectangular profile, the refined profile parameters is given by the equation:

$$P^R = (P^0, P^1, \ldots P^2) \begin{pmatrix} W_0 \\ W_1 \\ W_2 \end{pmatrix}. \qquad (3.60)$$

Figure 4C:
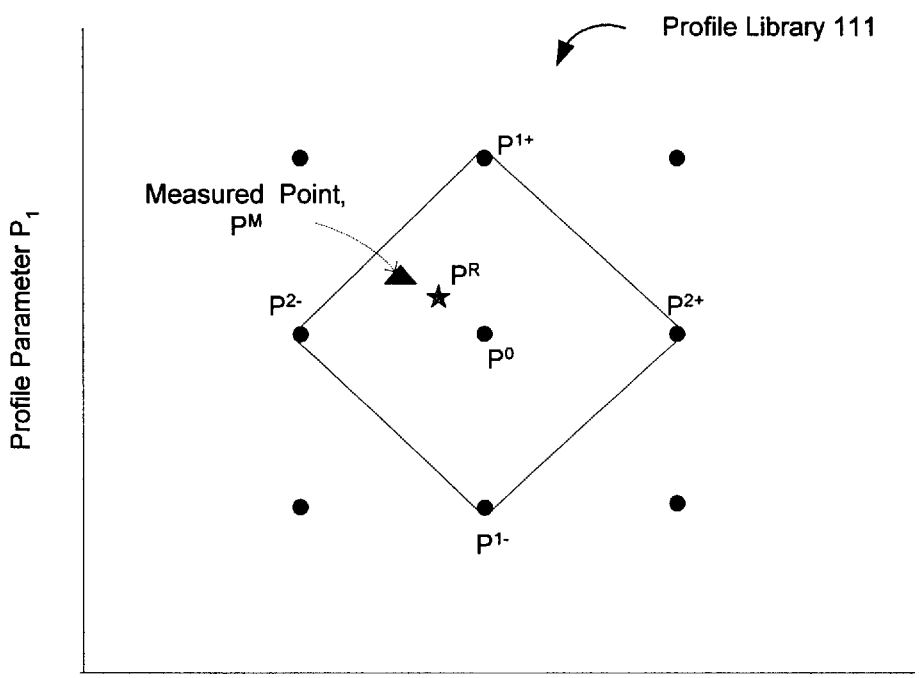

In another embodiment, a different polyhedron with a different number of corners is used. Referring to FIG. 4A, selection of the profile parameter data points for the polyhedron corners is done by selecting neighboring values of the profile parameters associated with the best match library spectrum 225. Referring to FIG. 4C, assume the rectangular structure profile of the previous example with the two profile parameters, namely, CD width, $P_1$, and height, $P_2$. Referring to FIG. 4C, $P^R$ is the refined or calculated parameter data point whereas $P^M$ is the actual parameter data point for the measured spectrum (not shown). The best match profile parameters point, $P^0$, associated with the best match spectrum $S^0$ (not shown), is the starting, point for selecting the other profile parameter data points. In the case of profile parameter $P_1$ in the Y-axis, both the neighboring values $P^{1+}$ in the positive direction and $P^{1-}$ in the negative direction of $P_1$ are selected. Similarly, both the neighboring $P^{2+}$ in the positive direction and $P^{2-}$ in the negative direction of $P_2$ in the X-axis are selected. The polyhedron is configured to include the measured point $P^M$ and the selected four neighboring values as corners. Regardless of the value of K, a similar set of steps is applied for selecting the neighboring data points of the profile parameters. The cost function of the best match spectrum relative to the measured diffracted spectrum and the cost function of the spectra associated with the selected data points relative to the measured diffracted spectrum are minimized by adjusting the weighting vector 235. In equation form:

$$\MIN_{W} C(W) \tag{4.00}$$

$$\text{such that } \sum_{i=1}^{K} W_i = 1 \tag{4.20}$$

and $$W_i \geq 0 \tag{4.40}$$

and where $$C(W) = \|[S^0, S^{1+}, S^{1-}, \ldots S^{2K}]_{N(2K+1)} W_{(2K+1)} - S^M\| \tag{4.60}$$

where:
C is the total cost function,
K is the number of profile parameter dimensions,
N is the number of spectrum data points for each measurement performed with the metrology device,
S is the diffracted spectrum, $S^0$ is the best-match spectrum, $S^{1+}$ is the spectrum associated with the chosen value of the first profile parameter in the positive direction, $S^{1-}$ is the spectrum associated with the chosen value of the first profile parameter in the negative direction, and so on up to $S^{2K}$, and $S^M$ is the measured spectrum, and
W is the weighting vector.

Optimization of the value of the weighting vector is subject to two constraints, namely, first, the sum of the weighting vectors must equal one and second, the value of the weighting vector may be equal or greater than zero. The refined profile parameters are calculated by using the weighting vector that minimized the total cost function 255. Continuing with the example of a rectangular profile, the refined profile parameters is given by the equation:

$$P^R = (P^0, P^{1+}, P^{1-}, P^{2+}, P^{2-}) \begin{pmatrix} W_0 \\ W_{1+} \\ W_{1-} \\ W_{2+} \\ W_{2-} \end{pmatrix} \tag{4.80}$$

where $P^R$ is a vector representing the refined profile parameters, $P^0$ is a vector representing the profile parameters of the best match spectrum, $P^{1+}$ and $P^{1-}$ are vectors representing the profile parameters of the first profile parameter in the positive and negative directions respectively, $P^{2+}$ and $P^{2-}$ are vectors representing the profile parameters of the second profile parameter in the positive and negative directions respectively, and so on, while $W_0$, $W_{1+}$, $W_{1-}$, $W_{2+}$, and $W_{2-}$ are the corresponding weighting factors of the profile parameter points.

Figure 5A:
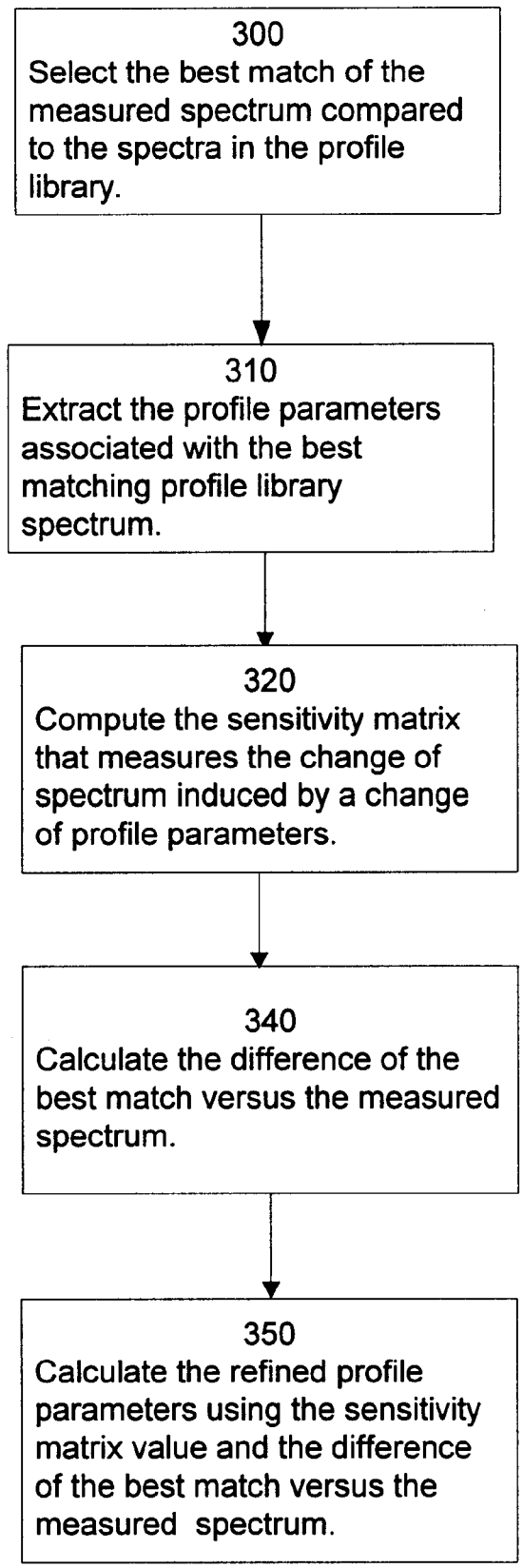
FIG. 5A is a flow chart of operational steps for profile refinement using sensitivity analysis in a preferred embodiment of the present invention.

FIG. 5A is a flow chart of operational steps for profile refinement using sensitivity analysis in a preferred embodiment of the present invention. The profile refinement process is performed after creating a library with a specified extent of non-linearity. The measured diffracted spectrum off a structure is compared to the spectra in the profile library and the best matching spectrum is selected 300. The profile parameters associated with the best matching profile library spectrum are extracted 310.

In an exemplary embodiment, a sensitivity matrix equation is used to find the adjustment value to convert the best matching profile parameters to the refined profile parameters. The basic equation for the sensitivity matrix J is:

$$J = \delta S/\delta P \tag{5.00}$$

where:
S is the diffracted spectrum measured by an optical metrology device,
$\delta S$ is the change of the diffracted spectrum induced by the change of P,
P represents profile parameters,
$\delta P$ is the change of the profile parameter value,
K is the number of profile parameter dimensions,
N is the number of spectrum data points for each measurement performed with the metrology device,
$S = (S_1, S_2, \ldots S_N)$, where $S_1$ the diffracted spectrum measured at measurement point 1, $S_2$ is the diffracted spectrum measured at measurement point 2, and so on, and
$P = (P_1, P_2, \ldots P_K)$ where $P_1$ is the first profile parameter, $P_2$ is for the second profile parameter, and so on. Expanding the sensitivity matrix equation yields:

$$J = \left[ \frac{\delta S^1}{\delta P_1}, \frac{\delta S^2}{\delta P_2}, \ldots \delta \frac{S^K}{\delta P_K} \right] \tag{5.20}$$

where $S^1$ is a column vector of length N, $S^2$ is a column vector of length N, etc.

The value of the sensitivity matrix J is calculated by changing one profile parameter by a small amount while keeping the others constant and calculating the incremental change in the spectrum as a result of the change in the profile parameter 320. This process is repeated for all the other profile parameters, the general equation as follows:

$$J_{ij} = \frac{\delta S_i}{\delta P_j} \tag{5.40}$$

where i is a spectrum data point for the measurement performed with the metrology device ranging from 1 to N, j is the a profile parameter dimension ranging from 1 to K, $J_{ij}$ is the value of the sensitivity matrix corresponding to the change in the profile parameter j, $\delta S^i$ is the change of the spectrum corresponding to change of the $\delta P_j$. $\delta S$ is the difference between the best match spectrum $S^0$ and S', where S' is the spectrum calculated using optical metrology simulation techniques for the value of the set of profile parameters taking into account the incremental change to one selected profile parameter. The process of calculating a spectrum using optical metrology simulation techniques is described in co-pending U.S. patent application Ser. No. 09/764,780 entitled "Caching of Intra-Layer Calculations for Rapid Rigorous Coupled-Wave Analyses" by Niu, et al., filed on Jan. 25, 2001 and is incorporated herein by reference.

Figure 5B:
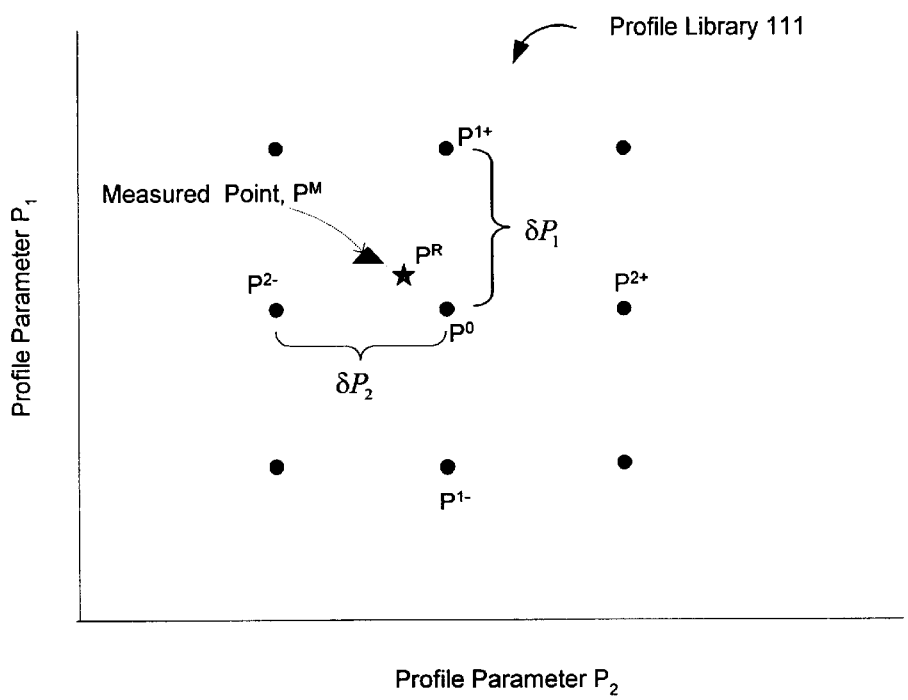
FIG. 5B is a graphical illustration of profile refinement utilizing sensitivity analysis in an exemplary embodiment of the present invention.

FIG. 5B is a graphical illustration of profile refinement utilizing sensitivity analysis in the present embodiment of the invention. Given a profile library 111 assuming a structure with two profile parameters, the figure includes a graph of profile parameters $P_1$ and $P_2$ in the Y-axis and X-axis respectively. Every data point in the graph represents a set of profile parameters with corresponding diffracted spectra (not shown.) For example, $P^0$ represents the profile parameters of the best match spectrum $S^0$, $P^M$ represents the profile parameters of the measured spectrum $S^M$, $P^{1+}$ represents the profile parameters of a neighboring data point in the positive direction of profile parameter $P_1$ of the spectrum $S^{1+}$, $P^{1-}$ represents the profile parameters of a neighboring data point in the negative direction of profile parameter $P_1$ of the spectrum $S^{1-}$, and so on. For this example and referring to FIG. 7B, $\delta P_1$ is the change of profile parameter $P_1$ when incremented in the positive direction and $\delta P_2$ is the change of profile parameter $P_2$ when incremented in negative direction. It is understood that the principles and concepts of the present invention applies to embodiments that have more than two profile parameters.

The difference between the best match spectrum, $S^0$, and the measured spectrum, $S^M$, is calculated 340. The refined profile parameters, $P^R$, are calculated using the sensitivity matrix value and the difference between the best match spectrum and the measured spectrum 350.

In an exemplary embodiment where the change of S induced by a change in P is linear, the $\delta S$ and $\delta P$ are approximated by $\Delta S$ and $\Delta P$ respectively. Using the basic sensitivity matrix equation and substituting $\Delta S$ and $\Delta P$ gives the equation:

$$\Delta S = J \Delta P \quad (5.60)$$

where:

$$\Delta S = (\Delta S_1, \Delta S_2 \ldots \Delta S_N), \quad (5.70)$$

$$\Delta P = (\Delta P_1, \Delta P_2 \ldots \Delta P_K). \quad (5.80)$$

$\Delta P$ is calculated by using the following equation:

$$\Delta P = (J^T J)^{-1} J^T \Delta S \quad (5.90)$$

where J is the sensitivity matrix calculated in the previous step and $\Delta S$ is the difference between the measured spectrum and the best match library spectrum. The value of the refined profile parameters PR is given by the equation:

$$P^R = P^0 + \Delta P \quad (6.00)$$

where $P^0$ represents the profile parameters associated with the best match spectrum and $\Delta P$ is the adjustment value derived from the previous step.

Figure 6:
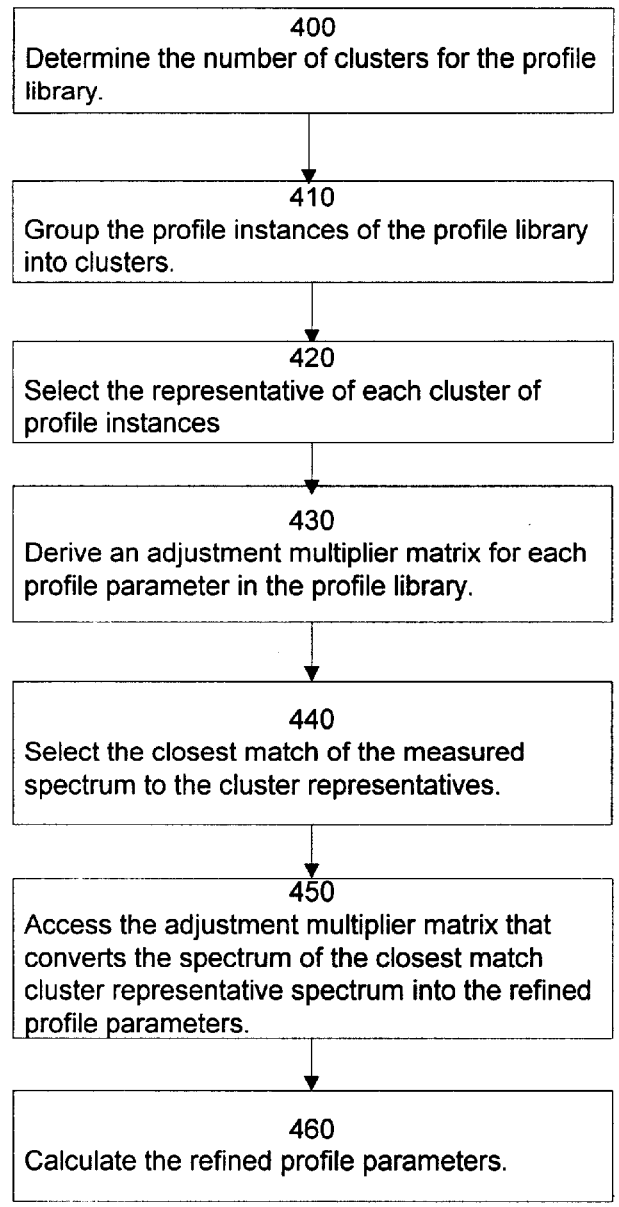
FIG. 6 is a flow chart of operational steps for profile refinement using clustering of the profile library instances in an exemplary embodiment of the present invention.

FIG. 6 is a flow chart of operational steps for profile refinement using clustering of the profile library instances in an exemplary embodiment of the present invention. As before, the profile refinement process is performed after creating a library with a specified extent of non-linearity. The number of clusters for the profile library is determined 400. Profile instances of the profile library are grouped into the number of clusters using a clustering algorithm 410. A representative of each profile cluster is selected 420. The process of clustering-profile library instances and selecting a representative of each profile cluster is described in co-pending U.S. patent application Ser. No. 09/737,705 entitled "Grating Profile Classification" by Doddi, et al., filed on Dec. 14, 2000, and is incorporated in its entirety herein by reference.

Still referring to FIG. 6, an adjustment multiplier matrix for each profile parameter in the profile library is derived 430. In some applications, the adjustment multiplier matrix is saved along with the selected cluster representatives. An exemplary embodiment is to solve for X in the following matrix equation:

$$AX = B \quad (7.00)$$

where:

A is a measured spectrum matrix of size n'xn, and each row of the matrix corresponds to one spectrum of the measured spectra, B is a profile parameter matrix of size n'xk and each row of the matrix corresponds to one profile parameter, k is the number of profile parameters, n is the number of points measured by the optical metrology device, n' is a number less than or equal to n, and X is the adjustment multiplier matrix of size nxk and each row of the matrix corresponds to one profile parameter.

The measured spectrum is compared to the spectra of the cluster representatives and the closest match is selected 440. The adjustment multiplier matrix associated with the closest matching cluster representative is accessed 450. Refined profile parameters are calculated using the adjustment multiplier matrix and the measured spectrum matrix 460. For example, assume the profile parameters k in a trapezoidal profile is equal to 3, namely, top CD, bottom CD, and height. Further assume the number of points measured in the range of wavelengths used by the metrology device is 53, the measured spectrum is H, the refined top CD is T, then T is equal to:

$$HX_{TOP-CD} = T \quad (7.20)$$

where $X_{TOP-CD}$ is a row of the adjustment multiplier matrix corresponding to the top CD, the adjustment multiplier matrix associated with the closest match cluster representative.

Figure 7:
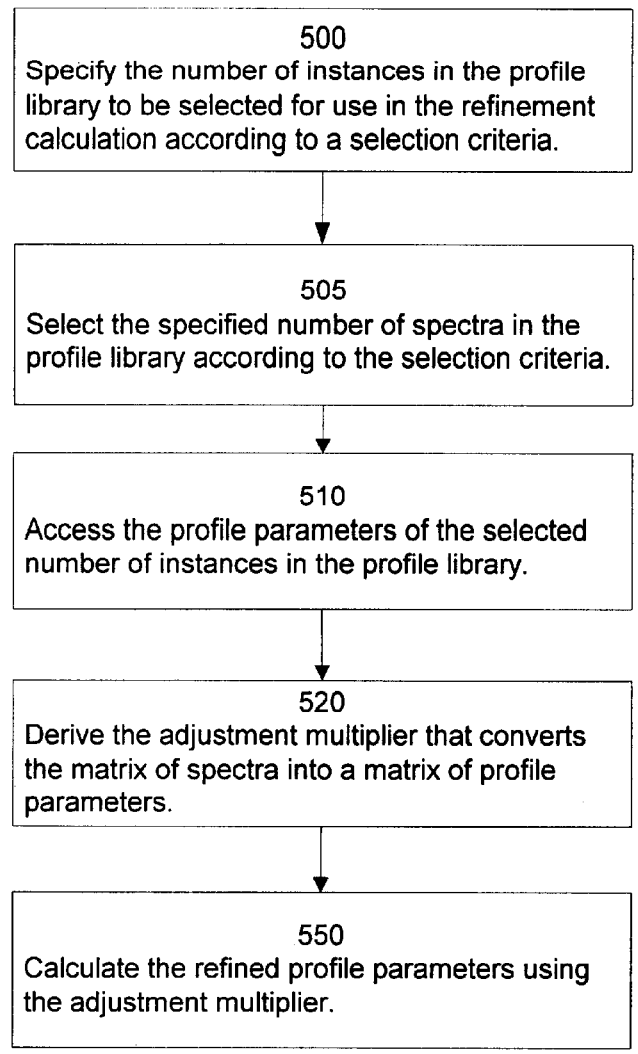
FIG. 7 is a flow chart of operational steps for profile refinement utilizing an adjustment multiplier and cost function optimization in an exemplary embodiment of the present invention.

FIG. 7 is a flow chart of operational steps for profile refinement utilizing an adjustment multiplier and cost function optimization in an exemplary embodiment of the present invention. As before, the profile refinement process is performed after creating a library with a specified extent of non-linearity. A number is specified that corresponds to the number of instances in the profile library that will be selected, according to selection criteria, for refinement calculation 500. The specified number may be varied from run to run. The specified number of library instances is selected using the selection criteria 505. Selection of specified number of profile library instances may be based on proximity to the measured spectrum. Alternatively, selection may be based on proximity to the best match spectrum. The profile parameters of the specified number of library spectra instances selected are accessed 510. The adjustment multiplier that converts the matrix of spectra into the matrix of profile parameters is derived 520. Refined profile parameters are calculated by multiplying the measured diffracted spectrum and the corresponding adjustment multiplier 530.

Figure 8:
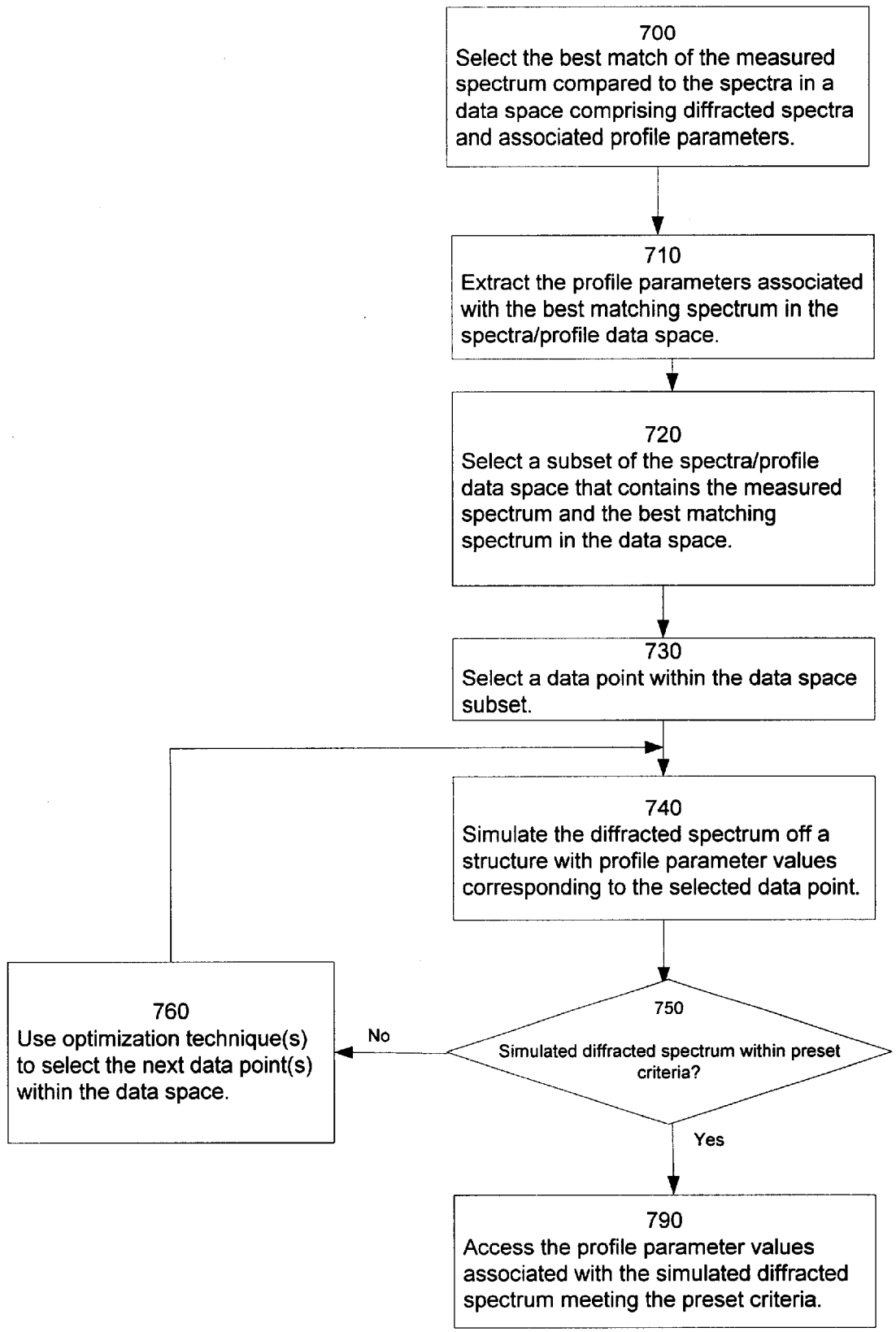
FIG. 8 is a flow chart of operational steps for profile refinement utilizing a regression-based method in an exemplary embodiment of the present invention.

FIG. 8 is a flow chart of operational steps for profile refinement utilizing a regression-based method in an exemplary embodiment of the present invention. As before, the profile refinement process is performed after creating a library with a specified extent of non-linearity. The measured diffracted spectrum off a structure is compared to the spectra in a data space comprising diffracted spectra and associated profile parameters where the best match spectrum in the data space is selected 700. The profile parameters associated with the best match spectrum in the data space is extracted 710. A subset of the data space that contains the measured diffracted spectrum and the best match spectrum is selected 720. The data space subset may be configured to resemble a shape such as a polyhedron, cube, or other three-dimensional shape. A data point within the data space subset is selected 730, the selected data point representing a set of associated profile parameters. A simulated diffracted spectrum off a structure with the profile parameters corresponding to the selected data point is calculated 740. An exemplary simulation of diffracted spectrum off a structure is described in co-pending U.S. patent application Ser. No. 09/764,780 entitled "Caching of Intra-Layer Calculations for Rapid Rigorous Coupled-Wave Analyses" by Niu, et al., filed on Jan. 25, 2001, and is incorporated in its entirety herein by reference.

Still referring to FIG. 8, the simulated diffracted spectrum is compared to the measured spectrum and the results are evaluated against preset criteria 750. For example, the preset criteria may be a preset error metric value or goodness of fit (GOF), or any measure of closeness of the simulated diffracted spectrum compared to the measured diffracted spectrum. One exemplary matching test that is well known in the art is the Minimum Least Squares Error algorithm. It is understood that other error metric algorithms may also be used. If the calculated error metric does not meet the preset criteria, then an optimization technique or techniques are used to select additional data points within the data space 760, and the calculation of the simulated diffracted spectrum is iterated. Exemplary optimization techniques include global optimization techniques such as simulated annealing and local optimization techniques such as the steepest descent algorithm. Use of optimization techniques to generate additional data points corresponding to structure profile parameters is described in co-pending U.S. patent application Ser. No. 09/923,578 entitled "Method and System of Dynamic Learning Through a Regression-Based Library Generation Process" by Niu, et al., filed on Aug. 6, 2001, and is incorporated in its entirety herein by reference.

Still referring to FIG. 8, the profile parameters associated with the simulated diffracted spectrum meeting the preset criteria is accessed, these values being the refined profile parameters 790.

Figure 9A:
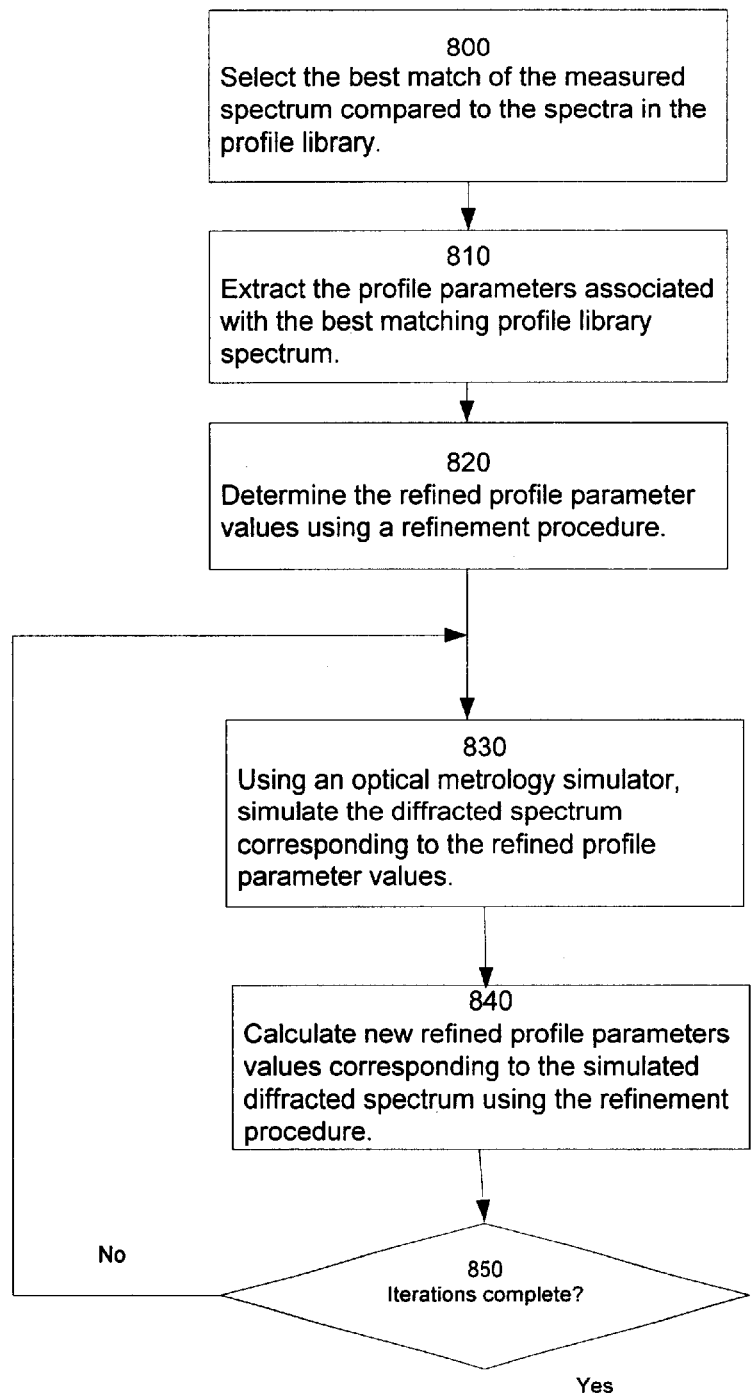
FIG. 9A is a flowchart of operational steps for profile refinement utilizing a localized fine-resolution refinement library method in an exemplary embodiment of the present invention.

FIG. 9A is a flow chart of operational steps for profile refinement utilizing a localized fine-resolution refinement library method in an exemplary embodiment of the present invention. Some refinement methods assume that the diffracted spectrum responds to changes in the profile parameters in a linear manner within the library data points. The present method corrects for the non-linearity effect. As such, the present method may be used with any profile library. The best match of the measured diffracted spectrum compared to the diffracted spectra in the profile library is selected 800. The profile parameters associated with the best matching profile library spectrum are extracted 810. Refined profile parameters are calculated using the procedure described below.

Figure 9B:
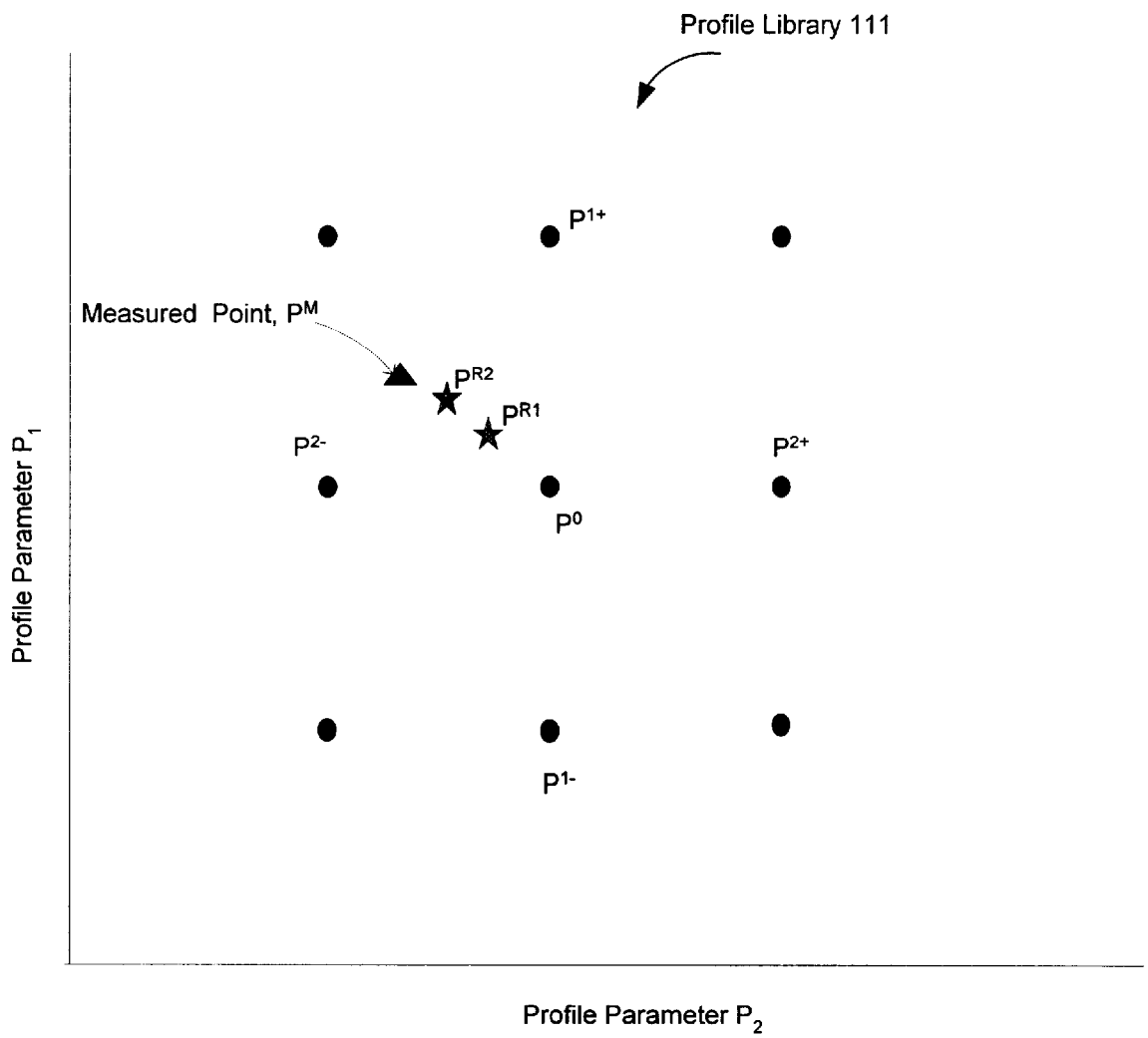
FIG. 9B is a graphical illustration of profile refinement utilizing a localized fine-resolution refinement library method in an exemplary embodiment of the present invention.

To illustrate the method, assume a 2-dimensional profile parameter space with $P_1$ and $P_2$ as the two dimensions as illustrated in FIG. 9B. The first refined profile parameter data point is determined from the equation 820:

$$P^{R1}=P^0+(J^TJ)^{-1}J^T(S^M-S^0) \qquad (7.40)$$

where $S^M$ is the measured spectrum, $P^{R1}$ is the first calculated refined profile parameters for the measured spectrum $S^M$, $P^0$ is the profile data point corresponding to the best match library spectrum $S^0$, and J is the sensitivity matrix derived in a similar manner as discussed in FIG. 5A. If the diffracted spectrum response to changes in the profile parameters were linear within the library data points, then the refined spectrum $S^R$ associated with $P^{R1}$ would be calculated with the following equation:

$$S^R=S^0+J(P^{R1}-P^0) \qquad (7.60).$$

However, due to the non-linearity effect, $S^R$ is not the "true number" or the accurate diffracted spectrum for profile parameter data point $P^{R1}$. In order to compensate for the non-linearity, an accurate calculation of the diffracted optical metrology spectrum for the set of profile parameters associated with $P^{R1}$ is performed using an optical metrology simulator 830, generating an accurate spectrum $S^{RA}$. The process of calculating a spectrum using optical metrology simulation techniques is described in co-pending U.S. patent application Ser. No. 09/764,780 entitled "Caching of Intra-Layer Calculations for Rapid Rigorous Coupled-Wave Analyses" by Niu, et al., filed on Jan. 25, 2001 and is incorporated herein by reference. The second calculated or revised refined profile parameter data point, $P^{R2}$, is calculated 840, using the equation:

$$P^{R2}=P^{R1}+(J^TJ)^{-1}J^T(S^M-S^{RA}) \qquad (7.80).$$

$(S_M-S^{RA})$ is less than $(S^M-S^0)$, thus the non-linearity effect is less and the refined profile parameter data point $P^{R2}$ is closer to the real profile parameters $P^M$ of the measured spectrum $S^M$. Referring to FIG. 9B, the data point $P^{R2}$ corresponding to $S^{RA}$ is closer to $P^M$ corresponding to the measured spectrum $S^M$.

Back to FIG. 9A, depending on user selected options, the simulation step 830 and the calculation of revised profile parameter data points 840 may be iterated a number of times 850. As number of iterations increases, the non-linearity effect is reduced, resulting in more accurate refined profile parameters.

Figure 10:
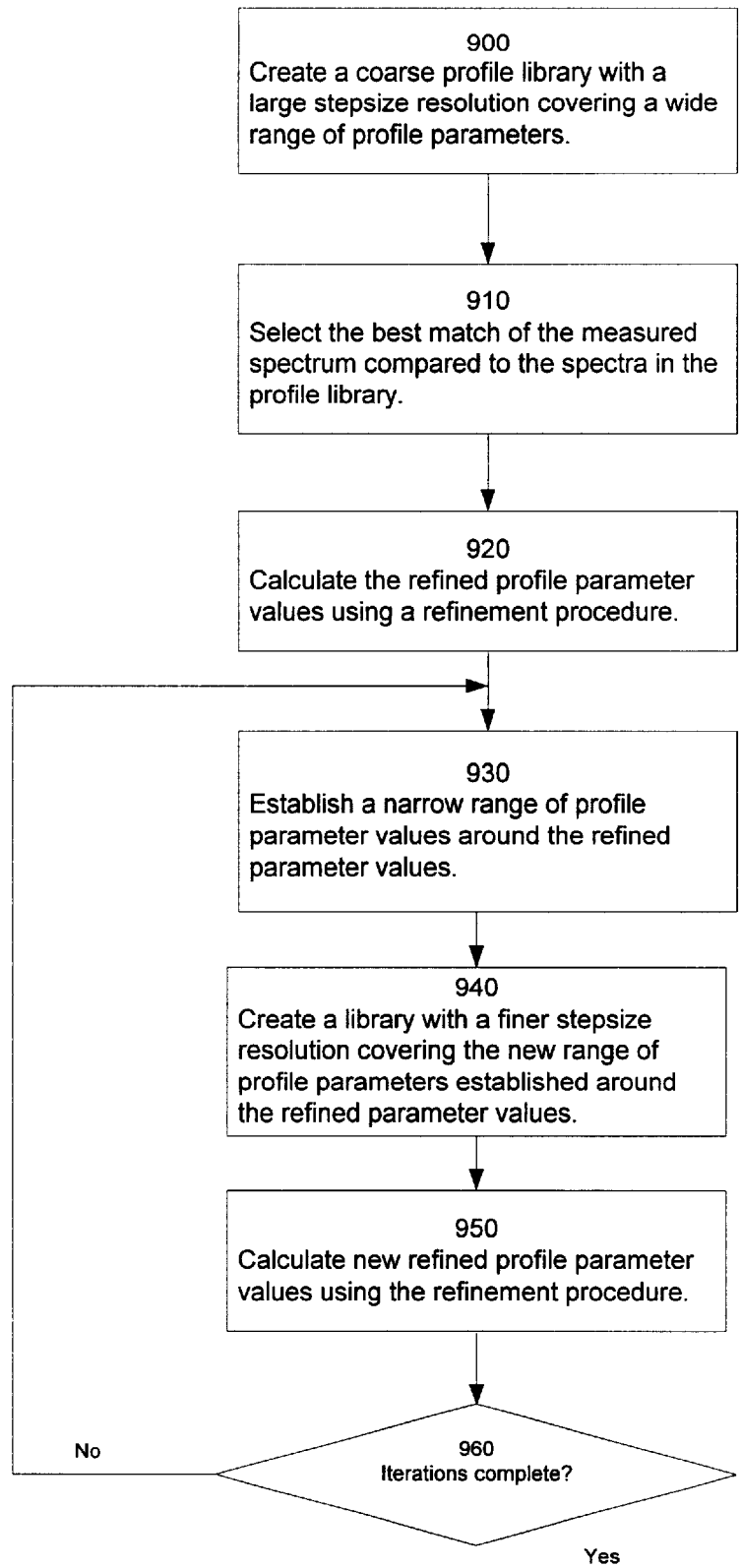
FIG. 10 is a flow chart of operational steps for profile refinement utilizing an iterative library refinement method in an exemplary embodiment of the present invention.

FIG. 10 is a flow chart of operational steps for profile refinement utilizing an iterative library refinement method in an exemplary embodiment of the present invention. A coarse resolution profile library, i.e., one created with a large stepsize resolution, covering a wide range of profile parameters is created 900. Given a measured spectrum, the best match of the measured spectrum compared to the spectra in the profile library is selected 910. The refined profile parameters are determined by using a refinement procedure 920. For the present embodiment, anyone of the previously discussed refinement methods or other commercially available refinements methods may be used. A new, narrower range of profile parameters is established around the refined profile parameters 930. The choice of the new, narrower range of the profile parameters is a user option. For example, for a trapezoidal profile with three profile parameters, namely, top CD, bottom CD, and height, the narrower top CD range may be one increment in the positive direction from the refined profile parameter value and one increment in the negative direction. The narrower range for the bottom CD may likewise be set to one increment in the positive direction and one increment in the negative direction, and so on. A profile library for the new range of profile parameters established around the refined profile values with a finer stepsize resolution is created 940. For example, the coarse library resolution may be 20 nanometers (nm). The first iteration of creating a finer stepsize resolution may result in a resolution of 15 nm, the second iteration may result in a resolution of 8 nm, and so on. The revised refined profile parameters are determined by using the same or a different refinement procedure 950 using the new successively finer stepsize-resolution libraries created. Depending on user selected options, the steps of establishing the profile parameter range, creating the new library, and calculating the revised refined profile parameters may be iterated a number of times 960. As the number of iterations increases, the library resolution increases in a progressively smaller space, resulting in more accurate refined profile parameters.

Figure 11:
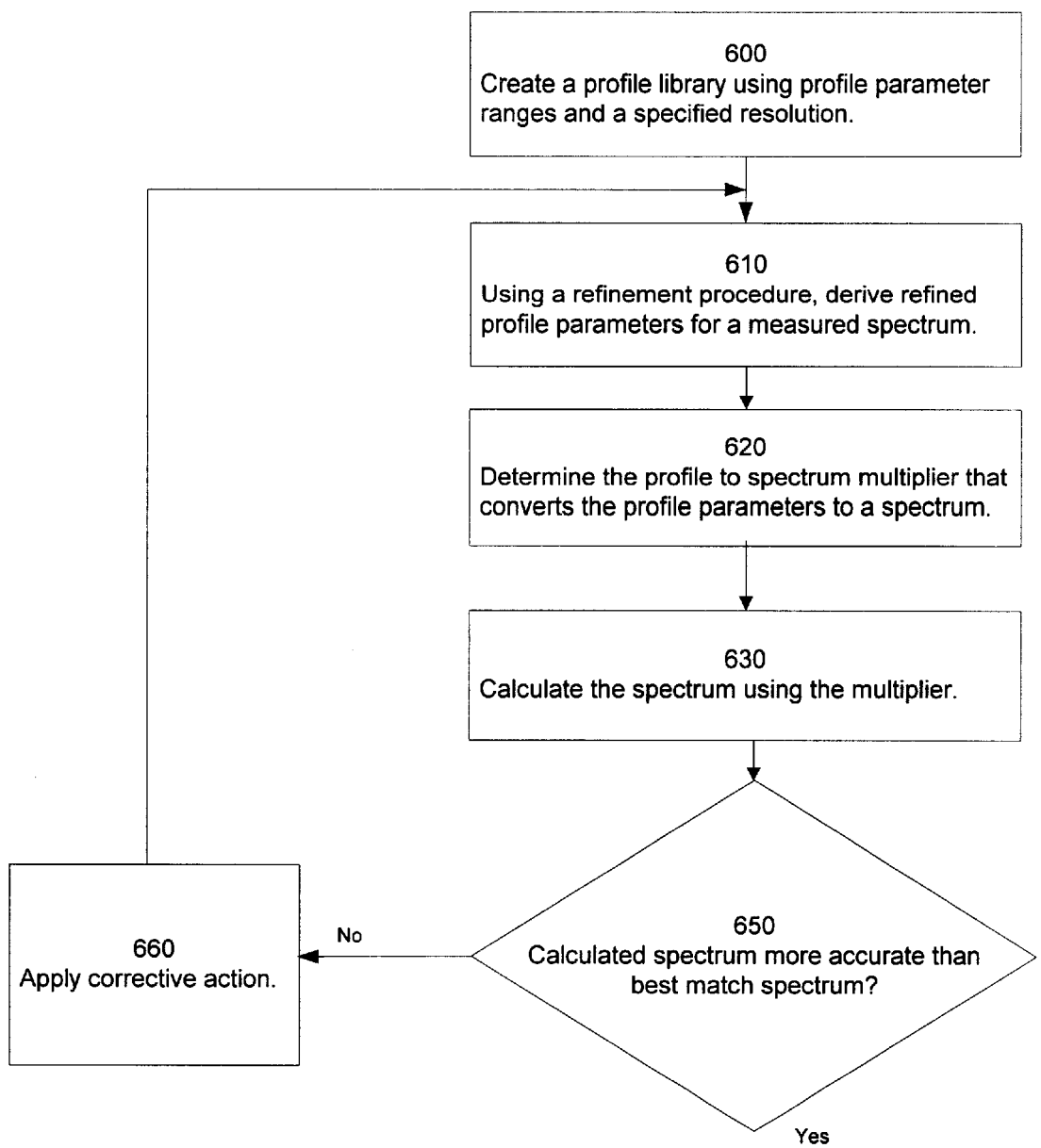
FIG. 11 is a flow chart of operational steps for verifying the accuracy of the refined profile parameter versus the best match profile parameter in an exemplary embodiment of the present invention.

FIG. 11 is a flow chart of operational steps for verifying the accuracy of the refined profile parameter versus the best match profile parameter in an exemplary embodiment of the present invention. Refinement accuracy checking is typically done during testing of refinement procedures and/or creation of the profile libraries. From specified ranges of the profile parameters and a given resolution, the profile library is created 600. Creation of a profile library is described in co-pending U.S. patent application Ser. No. 09/727,530 entitled "System and Method for Real-Time Library Generation of Grating Profiles" by Jakatdar, et al., filed on Nov. 28, 2000, and is incorporated in its entirety herein by reference.

A refinement calculation is performed using one or more of the refinement procedures and/or methods discussed above 610. A profile to spectrum multiplier Y that converts the refined profile parameters to refined spectra is determined 620. The adjustment multiplier from profile to spectrum is calculated using the basic equation (7.00) described in FIG. 6 and designating the adjustment multiplier matrix as Y. The refined diffracted spectrum is calculated using the profile to spectrum multiplier Y and the refined profile parameters 630 as expressed the following matrix equation:

$$EY=G \qquad (8.00)$$

where:

G is the refined spectra matrix of size 1xn, and each row of the matrix corresponds to one measurement of the measured spectrum, E is a refined profile parameter matrix of size 1xk and each row of the matrix corresponds to one profile parameter, k is the number of profile parameters, n is the number of points measured by the optical metrology device, and Y is the adjustment multiplier matrix of size kxn and each row of the matrix corresponds to one profile parameter.

The accuracy of the refined spectrum relative to the measured spectrum is compared to the accuracy of the best match spectrum relative to the measured spectrum 640. One method involves comparing the cost function of the refined spectrum relative to the best matching spectrum versus the cost function of the measured spectrum relative to the best matching spectrum. The cost function comparison is illustrated by the equations below.

Assume $V_1$ and $V_2$ are two vectors of size n, then the cost function of $V_1$ $$V_2 \text{ is: } Cost(V_1, V_2) = \sqrt{\sum_{i=1}^{n} (V_{1i} - V_{2i})^2}. \qquad (8.20)$$

A similar cost function can be calculated for $V_1$ relative to $V_3$, a third vector of size n.

It is understood that other cost optimization techniques may be used; furthermore, other techniques may also be used to compare relative accuracy of matrices and vectors. Still referring to FIG. 11, if the refined spectrum is more accurate than the best match spectrum 650, or a threshold goodness of fit is met, then the refinement setup is adequate.

For example, if $V_1$ is the measured spectrum, $V_2$ is the refined spectrum, and $V_3$ is the best match spectrum, then if $Cost(V_1,V_2)<Cost(V_1,V_3)$, the refinement setup is considered adequate. Otherwise, parameters of the library compilation are adjusted or a corrective action is applied 660 and the process is iterated starting at step 610. Several examples of corrective actions include recreating the profile library at a higher resolution or lowering the threshold deviation during the calculations of refined resolution. Alternatively, other refinement procedures described above or known in the trade may be used.

Figure 12:
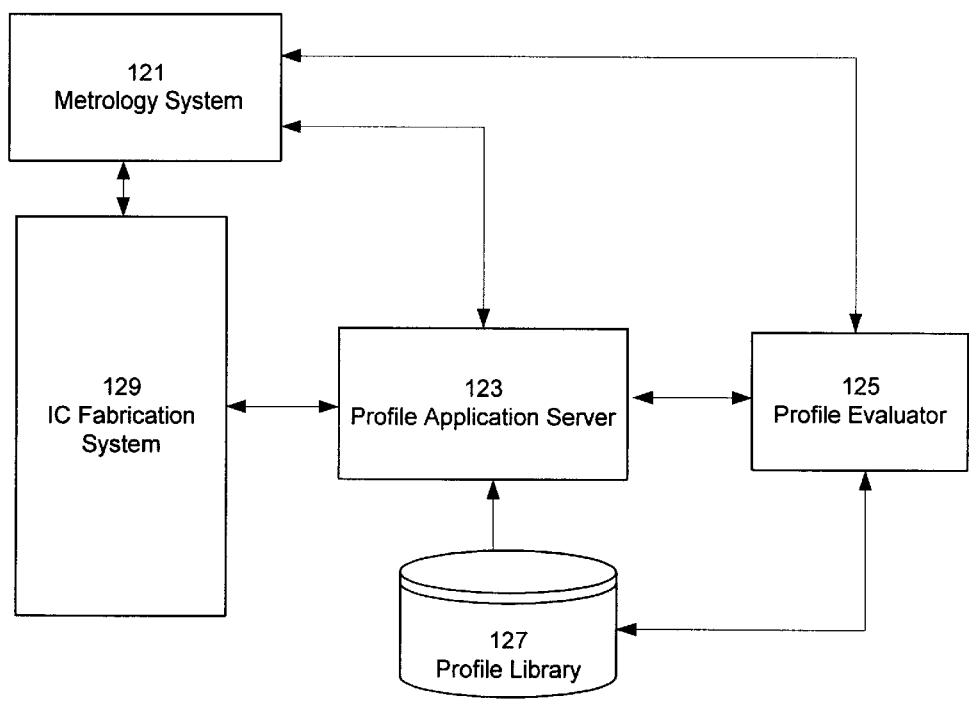
FIG. 12 is an architectural flow chart of a system including a profile evaluator in an exemplary embodiment of the present invention.

FIG. 12 is an architectural flow chart of a system including a profile evaluator in an exemplary embodiment of the present invention. An IC fabrication system 129 such as lithography, etch, or stripping unit is coupled to a metrology system 121. The metrology system may be an optical, electric, electron, or mechanical metrology system. Examples of optical metrology systems include scatterometric devices such as spectroscopic ellipsometers and reflectometers. Examples of electron metrology systems include CD-scanning electron microscope (CD-SEM), transmission electron microscope (TEM), and focused ion beam (FIB) devices. An example of a mechanical metrology system includes an atomic force microscope (AFM) whereas an example of an electric metrology system includes a capacitance-measuring unit. The metrology system 121 is coupled to a profile application server 123 and alternatively to a profile evaluator 125. The metrology system 121 measures an IC structure and generates a measured signal and transmits the measured signal to the profile application server 123. The profile application server 123 accesses the profile library 127 in order to find the best match signal in the profile library 127. If predetermined criteria of acceptability are not met, for example, an error metric is not met, then the profile evaluator 125 is invoked. Alternatively, the profile evaluator 125 may be invoked based on some other criteria or invoked automatically by the profile application server 123. In some applications, the profile evaluator 125 may be invoked automatically and/or directly by the metrology system 121. The profile evaluator 125 either accesses the profile library 127 directly or through the profile application server 123. The profile evaluator 125 transmits the refined profile parameters back to the profile application server 123 and the profile application server 123 in turn makes the information available to the IC fabrication system 129. Alternatively, the profile evaluator 125 transmits the refined profile parameters back to the metrology system 121. The profile library 127 may be a physical library in a storage device or a data store in a computer memory or a data store in a storage device. Refined profile parameters are profile parameters calculated using refinement methods and procedures, several of which are described below. A profile evaluator 125 is a device, software, or firmware capable of executing the refinement methods and procedures.

Figure 13A:
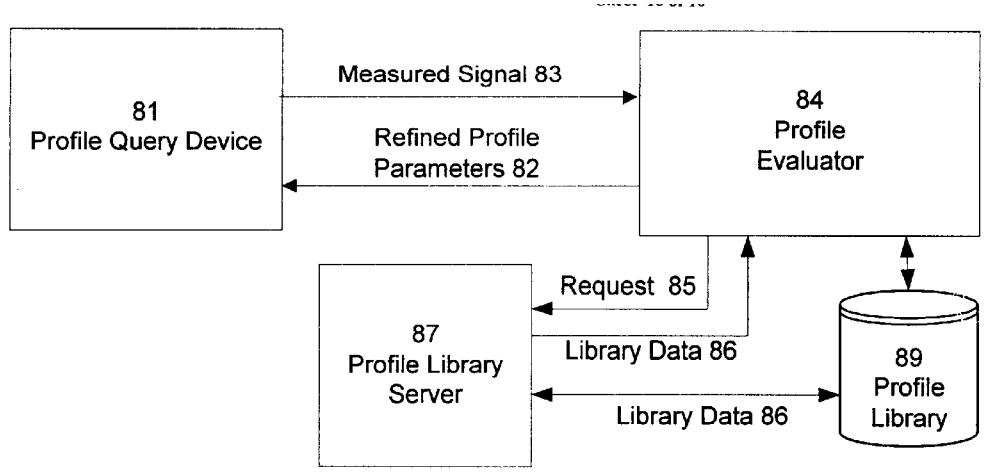
FIG. 13A is an architectural diagram illustrating a query device coupled to a profile evaluator in an exemplary embodiment of the present invention.

FIG. 13A is an architectural diagram illustrating a query device coupled to a profile evaluator in an exemplary embodiment of the present invention. A profile query device 81 interacts with a profile evaluator 84 to determine the refined profile parameters corresponding to measured signal 83. The query from the profile query device 81 may be activated automatically or as a result of a matching process of the measured signal 83 compared to signals in the profile library 89 where an error metric criterion is not met. The closest or best match library signal is one that minimizes the error between the measured signal and the profile library signal. One error metric that produces appropriate results is the sum-of-squared-difference error, where the error between the measured signal and the profile library signal is minimized. It is understood that other error metrics may produce equally appropriate results. The profile query device 81 may also invoke the profile evaluator 84 based on a hardware, firmware, or software request. The profile query device 81 may be a microcontroller, computer, or IC fabrication equipment with an integrated control unit capable of sending the measured signal 83 to the profile evaluator 84 and capable of receiving the refined profile parameters 82. In an exemplary embodiment, the profile evaluator 84 transmits a request 85 to a profile library server 87 for library data 86 to be used in the refinement processing. Acting on the request, profile, library server 87 accesses a profile library 89 comprising signals and profile data and transmits these library data 86 to the profile evaluator 84. In an alternate embodiment, the profile evaluator 84 directly accesses a profile library 89 for the profile and signal data needed for refinement processing.

Figure 13B:
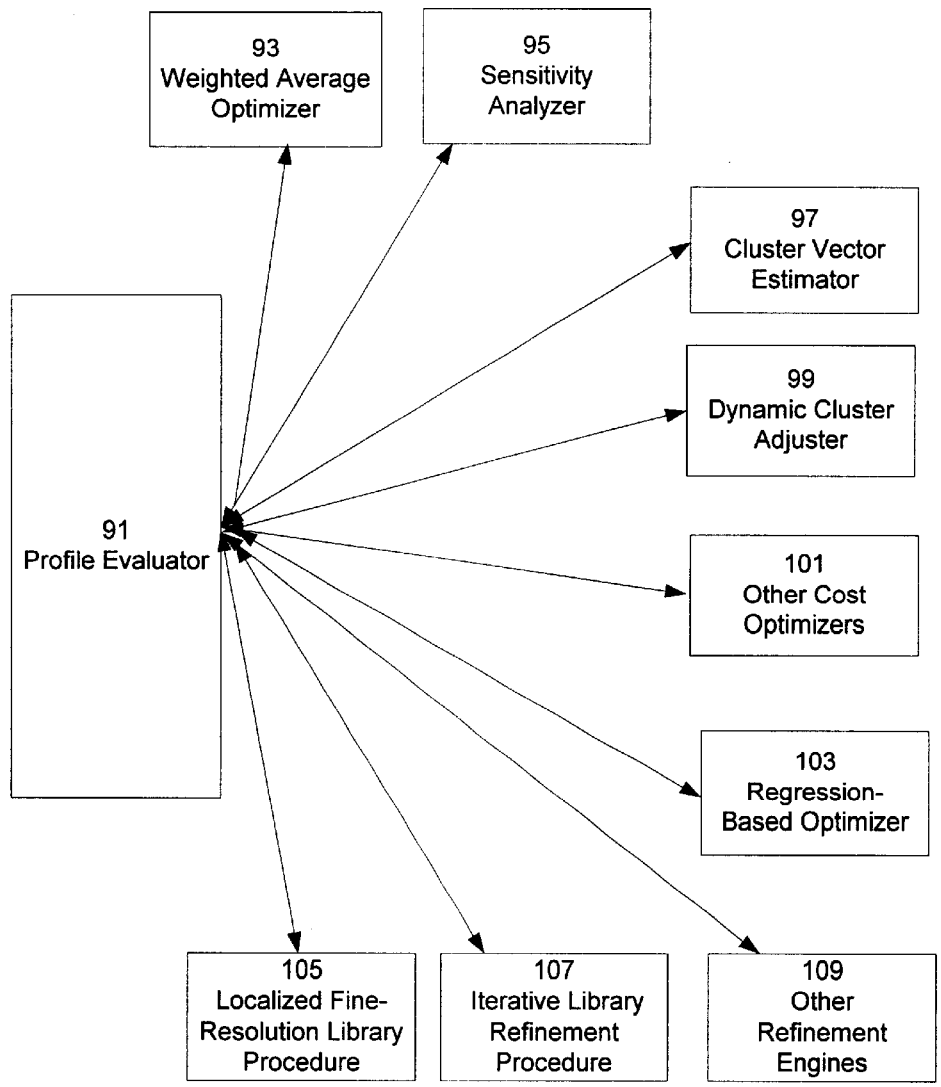
FIG. 13B is an architectural diagram illustrating a profile evaluator invoking various cost optimizers and refinement engines in exemplary embodiments of the present invention.

FIG. 13B is an architectural diagram illustrating a profile evaluator invoking various refinement engines in exemplary embodiments of the present invention. The profile evaluator 91 may activate one or more types of refinement engines to get the desired refinement results based on specified acceptance criteria. A refinement engine may be a software, firmware, or hardware capable of performing the operational steps of refinement given measured signals and a data space comprising signals and associated profile parameters. A weighted average optimizer 93, sensitivity analyzer 95, cluster vector estimator 97, dynamic cluster adjuster 99, or other cost function optimizers 101 may be used to generate the refined profile parameters using measured signals and a set of signals and associated profile parameters. A regression-based optimizer 103 may be used wherein data points within a data space of signals and profile parameters are successively evaluated for goodness of fit compared to the measured spectrum.

Alternatively, the profile evaluator 91 may activate a refinement engine using a localized fine-resolution library procedure 105 or an iterative library refinement procedure 107. Other refinement engines 109 may use a refinement technique such as bilinear refinement, Lagrange refinement, Cubic Spline refinement, Aitken refinement, weighted average refinement, multi-quadratic refinement, bi-cubic refinement, Turran refinement, wavelet refinement, Bessel's refinement, Everett refinement, finite-difference refinement, Gauss refinement, Hermite refinement, Newton's divided difference refinement, osculating refinement, Thiele's refinement algorithm or other refinement algorithms.

The profile evaluator generally require a specified extent of non-linearity between profile parameter and spectrum data points in order to generate refined profile parameters of structures that provide a specified level of accuracy. To achieve consistent results, a linearity test or procedure is required. The extent of non-linearity between profile library data points can be ensured by either empirical methods or by the use of mathematical algorithms.

Foregoing described embodiments of the invention are provided as illustrations and descriptions. They are not intended to limit the invention to precise form described. For example, as discussed above, the concepts and principles of the present invention will apply to other refinement algorithms, procedures, and/or methods. Furthermore, as discussed in FIG. 12, the concepts and principles of the present invention apply to many types of metrology devices that measure signals off an IC structure and correlate the signals to profiles of the structures. The principles of refinement discussed above equally apply to situations where a profile library exists or where there is no preexisting profile library. Where there is no preexisting profile library, a signal simulator may be used to calculate the data points for a data space of signals and corresponding profile parameters, the data space thus replacing the function of the profile library. In addition to optical metrology simulators, other metrology simulators perform similar functions as the optical metrology simulator in simulating the signals for a set of profile parameters.

In particular, it is contemplated that functional implementation of the present invention described herein may be implemented equivalently in hardware, software, firmware, and/or other available functional components or building blocks. Other variations and embodiments are possible in light of above teachings, and it is thus intended that the scope of invention not be limited by this Detailed Description, but rather by Claims following.

We claim:

1. A method of determining the profile of an integrated circuit structure from a measured signal, the method comprising:

measuring a signal off a structure with a metrology device, the measurement generating a measured signal;

selecting a best match of the measured signal in a profile data space, the profile data space having data points with a specified extent of non-linearity, the data points representing profile parameters and associated signals, the profile parameters characterizing the profile of the integrated, circuit structure, the best match being a data point of the profile data space with a signal closest to the measured signal; and determining refined profile parameters corresponding to the measured signal based on the profile parameters of the selected signal using a refinement procedure;

wherein the refinement procedure comprises a series of steps designed to determine refined profile parameters using the measured signal, data associated with the best match signal, and other data from and/or derived from the profile data space.

2. The method of claim 1 wherein selecting the best match of the measured signal in the profile data space, the data space having data points with the specified extent of non-linearity comprises:

specifying the extent of non-linearity between data points of the profile data space; and verifying that the specified extent of non-linearity exists between the data points of the profile data space.

3. The method of claim 2 wherein specifying the extent of non-linearity between data points of the profile data space comprises establishing a threshold deviation for each profile parameter.

4. The method of claim 2 wherein verifying that the specified extent of non-linearity exists between the data points of the profile data space comprises:

calculating a refined resolution of data points in the profile data space, the refined resolution designed to ensure that the specified extent of non-linearity exists between the data points; and creating the data points of the profile data space using the calculated refined resolution.

5. The method of claim 4 wherein calculating the refined resolution of data points in the profile data space comprises:

calculating a sensitivity matrix, the sensitivity matrix being a measure of change of the signal induced by a change in the profile parameter;

determining a maximum refined resolution for each profile parameter while maintaining the associated extent of non-linearity between data points of the profile data space.

6. The method of claim 1 wherein the metrology device is an optical metrology device, an electron metrology device, an electrical metrology device or a mechanical metrology device.

7. The method of claim 1 wherein determining refined profile parameters corresponding to the measured signal comprises:
   selecting a polyhedron in the profile data space, the polyhedron containing the best match data point and having corners corresponding to selected profile parameter data points proximate to the best match data point; and
   minimizing a total cost function, the total cost function comprising a cost function of the signals corresponding to the selected profile parameter data points relative to the measured signal and a cost function of the best match signal relative to the measured signal.

8. The method of claim 7 wherein the selected polyhedron has one corner associated with each profile parameter.

9. The method of claim 7 wherein the selected polyhedron has two corners associated with each profile parameter.

10. The method of claim 7 wherein minimizing the, total cost function comprises:
    selecting a set of weighting vectors, each weighting vector having vector elements, each vector element associated with the signal corresponding to a selected data point;
    calculating the total cost function for each weighting vector of the set of weighting vectors; and
    selecting the weighting vector that yields the minimum total cost function.

11. The method of claim 10 further comprising:
    calculating the refined profile parameters using the weighting vector associated with the minimum total cost function.

12. The method of claim 1 wherein determining refined profile parameters corresponding to the measured signal comprises:
    computing a sensitivity matrix, the sensitivity matrix being a measure of the change of the signal induced by a change of the profile parameters;
    determining an adjustment value of the profile parameters using the computed sensitivity matrix, and
    calculating the refined profile parameters by adding the adjustment value of the profile parameters to corresponding profile parameters of the best match data point in the profile data space.

13. The method of claim 12 wherein determining the adjustment value of the profile parameters comprises:
    calculating the difference of the best match signal from the measured signal;
    calculating the adjustment value using the difference of the best match signal from the measured signal and the calculated sensitivity matrix.

14. The method of claim 1 wherein the refinement procedure to determine the refined profile parameters utilizes bilinear refinement, Lagrange refinement, Cubic Spline refinement, Aitken refinement, weighted average refinement, multi-quadratic refinement, bi-cubic refinement, Turran refinement, wavelet refinement, Bessel's refinement, Everett refinement, finite-difference refinement, Gauss refinement, Hermite refinement, Newton's divided difference refinement, osculating refinement, or Thiele's refinement algorithm.

15. A method of determining the profile of an integrated circuit structure from a measured signal, the method comprising:
    measuring a signal off a structure with a metrology device, the measurement generating a measured signal;
    selecting a best match of the measured signal by comparing the measured signal to signals of cluster representatives, the cluster representatives selected from clusters of data points of a profile data space, the cluster representatives having an associated adjustment multiplier matrix configured to convert signals to profile parameters, the data points of the profile data space having a specified extent of non-linearity, the data points representing profile parameters and associated signals, the profile parameters characterizing the profile of the integrated circuit structure; and
    calculating refined profile parameters by multiplying the measured signal and an adjustment multiplier matrix.

16. The method of claim 15 wherein selecting the best match of the measured signal by comparing the measured signal to signals of cluster representatives comprises:
    grouping data points of the profile data space into the clusters;
    selecting the cluster representative for each cluster; and
    deriving the adjustment multiplier matrix for each profile parameter of the cluster representative of each cluster.

17. The method of claim 15 further comprising:
    testing the accuracy of the refined profile parameters versus the profile parameters of the best match signal against preset standards; and
    applying a corrective action if the refined profile parameters do not meet the preset standards.

18. A method of determining the profile of an integrated circuit structure from a measured signal, the method comprising:
    measuring a signal off a structure with a metrology device, the measurement generating a measured signal;
    selecting a specified number of data points of a data space closest to the measured signal, the data points of the data space representing profile parameters and associated signals, the profile parameters characterizing the profile of the integrated circuit structure, the data points of the data space having a specified extent of non-linearity;
    deriving an adjustment multiplier, the adjustment multiplier configured to convert signals associated with the selected number of data points to corresponding profile parameters; and
    calculating refined profile parameters corresponding to the measured signal by multiplying the measured signal and the adjustment multiplier.

19. A method of determining the profile of an integrated circuit structure from a measured signal, the method comprising:
    measuring a signal off a structure with a metrology device, the measurement generating a measured signal;
    selecting a best match of the measured signal in a profile data space, the profile data space having data points with a specified extent of non-linearity, the data points representing profile parameters and associated signals, the profile parameters characterizing the profile of the integrated circuit structure, the best match being a data point of the profile data space with a signal closest to the measured signal;
    selecting a specified number of data points closest to the best match;
    deriving an adjustment multiplier by using data associated with the selected data points, the adjustment multiplier configured to convert signals of the selected data points to corresponding profile parameters; and calculating refined profile parameters corresponding to the measured signal by multiplying the measured signal and the adjustment multiplier.

20. A method of adjusting the parameters of profile refinement for use in determining the profile of an integrated circuit structure, the method comprising:

determining refined profile parameters corresponding to a measured signal by using a refinement procedure and a profile data space created at a specified resolution, the profile data space having data points, the data points representing profile parameters and associated signals, the profile parameters characterizing the profile of the integrated circuit structure;

deriving a multiplier for converting the profile parameters to a corresponding calculated signal, the derivation using data associated with selected data points;

calculating a signal using the multiplier and the refined profile parameters of the measured signal;

comparing the goodness of fit of the calculated signal relative to the measured signal versus the goodness of fit of a best match signal from the profile data space relative to the measured signal, the best match signal obtained by comparing the measured signal to signals associated with data points of the profile data space; and selecting a calculated signal closest to the measured signal;

wherein the refinement procedure comprises a series of steps designed to determine refined profile parameters using the measured signal, data associated with the best match signal, and other data from and/or derived from the profile data space.

21. The method of claim 20 wherein comparing the goodness of fit comparison is performed by comparing the cost function of the calculated signal relative to the measured signal versus the cost function of the best match signal relative to the measured signal.

22. The method of claim 20 further comprising:

implementing a corrective action to improve the goodness of fit of the calculated signal relative to the measured signal.

23. The method of claim 22 wherein implementing the corrective action comprises recreating the profile data space at a higher resolution than the original resolution.

24. The method of claim 20 wherein the implementing the corrective action comprises changing the refinement procedure to a different refinement procedure.

25. A method of determining the profile of an integrated circuit structure from a measured signal, the method comprising:

measuring a signal off a structure with a metrology device, the measurement generating a measured signal;

selecting a best match of the measured signal in a profile data space, the data points representing profile parameters and associated signals, the profile parameters characterizing the profile of the integrated circuit structure, the best match being a data point of the profile data space with a signal closest to the measured signal;

selecting a first data point within a subset of the profile data space, the profile data space subset containing the measured signal and data points proximate to the data point associated with the best match signal;

simulating a signal off a structure with profile parameters corresponding to the selected first data point;

verifying that a profile refinement preset criteria is met, the profile refinement preset criteria comprising a measure of goodness of fit of the simulated signal relative to the measured signal; and extracting profile parameters associated with the simulated signal that meet the profile refinement preset criteria.

26. The method of claim 25 wherein verifying that the profile refinement preset criteria is met comprises:

testing if an error metric is within the profile refinement preset criteria, the error metric measuring the goodness of fit of the simulated signal relative to the measured signal; and if the error metric is outside of the profile refinement preset criteria, performing an optimization technique to select the next data point within the data space subset, the next data point used to determine the next simulated signal.

27. The method of claim 26 wherein performing the optimization technique to select the next data point within the data space subset involves applying a global optimization technique and/or a local optimization technique.

28. The method of claim 25 wherein the profile data space is populated with data points generated by a metrology simulation process, the metrology simulation process calculating signals off structures from sets of profile parameters.

29. A method of determining the profile of an integrated circuit structure from a measured signal, the method comprising:

measuring a signal off a structure with a metrology device, the measurement generating a measured signal;

selecting a best match of the measured signal in a profile data space, the data points representing profile parameters and associated signals, the profile parameters characterizing the profile of the integrated circuit structure, the best match being a data point of the profile data space with a signal closest to the measured signal;

calculating a sensitivity matrix, the sensitivity matrix being a measure of the change of the signal induced by a change of the profile parameters;

determining a first set of refined profile parameters using the calculated sensitivity matrix and the best match profile parameters;

simulating a first signal using the first set of refined profile parameters; and determining a second set of refined profile parameters using the calculated sensitivity matrix and the first set of refined profile parameters.

30. The method of claim 29 further comprising:

simulating a second signal using the second set of refined profile parameters; and determining a third set of refined profile parameters using the calculated sensitivity matrix and the second set of refined profile parameters.

31. A method of determining the profile of an integrated circuit structure from a measured signal, the method comprising:

measuring a signal off a structure with a metrology device, the measurement generating a measured signal;

selecting a best match of the measured signal in a profile data space, the data points representing profile parameters and associated signals, the profile parameters characterizing the profile of the integrated circuit structure, the best match being a data point of the profile data space with a signal closest to the measured signal;

determining a first set of refined profile parameters using a refinement procedure, the refinement procedure being a series of steps designed to determine refined profile parameters using the measured signal, data associated with the best match signal, and other data from and/or derived from the profile data space;

establishing ranges of the profile parameters around the first set of refined profile parameters;

creating a second profile data space using the ranges established around the first set of refined profile parameters; and determining a second set of refined profile parameters using the refinement procedure;

wherein the refinement procedure comprises a series of steps designed to determine refined profile parameters using the measured signal, data associated with the best match signal, and other data from and/or derived from the profile data space.

32. The method of claim 31 further comprising:

creating a third profile data space using the ranges established around the second set of refined profile parameters; and determining a third set of refined profile parameters using the refinement procedure.

33. A method of determining the profile of an integrated circuit structure from a measured diffracted spectrum, the method comprising:

measuring a diffracted spectrum off a structure with a metrology device, the measurement generating a measured diffracted spectrum;

selecting a best match of the measured diffracted spectrum in a profile library, the profile library having instances with a specified extent of non-linearity, the profile library instances including profile parameters and associated diffracted spectrum, the profile parameters characterizing the profile of the integrated circuit structure, the best match being an instance of the profile library with diffracted spectrum closest to the measured diffracted spectrum; and determining refined profile parameters corresponding to the measured signal based on the profile parameters of the selected signal using a refinement procedure;

wherein the refinement procedure comprises a series of steps designed to determine refined profile parameters using the measured signal, data associated with the best match signal, and other data from and/or derived from the profile data space.

34. The method of claim 33 wherein selecting a best match of a measured diffracted spectrum in the profile library comprises:

specifying the extent of non-linearity between instances of the profile library; and verifying that the specified extent of non-linearity exists between the instances of the profile library.

35. The method of claim 34 wherein specifying the extent of non-linearity comprises establishing a threshold deviation for each profile parameter.

36. The method of claim 34 wherein verifying that the specified extent of non-linearity exists between the instances of the profile library comprises:

calculating a refined resolution of instances in the profile library, the refined resolution designed to ensure that the specified extent of non-linearity exists between the instances in the profile library; and creating the profile library using profile parameter ranges and the calculated refined resolution.

37. The method of claim 36 wherein calculating the refined resolution of instances in the profile library comprises:

calculating a sensitivity matrix, the sensitivity matrix being a measure of change of the signal induced by a change in the profile parameter;

determining a maximum refined resolution for a profile parameter while maintaining the specified extent of non-linearity between instances of the profile library.

38. The method of claim 33 wherein determining refined profile parameters corresponding to the measured signal comprises:

selecting a polyhedron in a profile data space, the profile data space having data points representing instances of the profile library, the polyhedron containing the best match data point and having corners corresponding to selected data points proximate to the best match data point, the best match data point corresponding to the best match instance of the profile library; and minimizing a total cost function, the total cost function comprising a cost function of the diffracted spectrum corresponding to the selected data points relative to the measured diffracted spectrum and a cost function of the best match diffracted spectrum relative to the measured diffracted spectrum.

39. The method of claim 38 wherein the selected polyhedron has one corner associated with each profile parameter.

40. The method of claim 38 wherein the selected polyhedron has two corners associated with each profile parameter.

41. The method of claim 38 wherein minimizing the total cost function comprises:

selecting a set of weighting vectors, each weighting vector having vector elements, each vector element associated with the diffracted spectrum corresponding to a selected data point;

calculating the total cost function using a weighting vector of the set of weighting vectors; and selecting the weighting vector associated with the minimum total cost function.

42. The method of claim 41 further comprising:

calculating the refined profile parameters using the weighting vector associated with the minimum total cost function.

43. The method of claim 33 wherein determining refined profile parameters corresponding to the measured signal comprises:

computing a sensitivity matrix, the sensitivity matrix being a measure of the change of the signal induced by a change of the profile parameters;

determining an adjustment value of the profile parameters using the sensitivity matrix; and calculating the refined profile parameters by adding the adjustment value of the profile parameters to corresponding profile parameters of the best match instance in the profile library.

44. The method of claim 43 wherein the determining the adjustment value of the profile parameters comprises:

calculating the difference of the best match spectrum from the measured signal; and calculating the adjustment value using the difference of the best match spectrum from the measured spectrum and the calculated sensitivity matrix.

45. The method of claim 33 wherein the refinement procedure to determine the refined profile parameters utilizes bilinear refinement, Lagrange refinement, Cubic Spline refinement, Aitken refinement, weighted average refinement, multi-quadratic refinement, bi-cubic refinement, Turran refinement, wavelet refinement, Bessel's refinement, Everett refinement, finite-difference refinement, Gauss refinement, Hermite refinement, Newton's divided difference refinement, osculating refinement, or Thiele's refinement algorithm.

46. A method of determining the profile of an integrated circuit structure from a measured diffracted spectrum, the method comprising:

measuring a diffracted spectrum off a structure with a metrology device, the measurement generating a measured diffracted spectrum;

selecting a best match of the measured diffracted spectrum by comparing the measured diffracted spectrum to diffracted spectra of cluster representatives, the cluster representatives having an associated adjustment multiplier matrix configured to convert the diffracted spectrum to profile parameters, the cluster representatives selected from clusters of instances of a profile library, the instances of the profile library including diffracted spectrum and profile parameters, the profile parameters characterizing the profile of the integrated circuit structure, the instances of the profile library created with a specified extent of non-linearity; and calculating refined profile parameters by multiplying the measured diffracted spectrum and the adjustment multiplier matrix.

47. The method of claim 46 wherein selecting the best match of the measured diffracted spectrum by comparing the measured diffracted spectrum to diffracted spectra of cluster representatives comprises:

grouping instances of the profile library into the clusters;

selecting the cluster representative for each cluster; and deriving the adjustment multiplier matrix for each profile parameter value of the cluster representative of each cluster.

48. The method of claim 46 further comprising:

testing the accuracy of the refined profile parameters versus the profile parameters of the best match signal against preset standards; and applying a corrective action if the refined profile parameters do not meet the preset standards.

49. A method of determining the profile of an integrated circuit structure from a measured diffracted spectrum, the method comprising:

measuring a diffracted spectrum off a structure with a metrology device, the measurement generating a measured diffracted spectrum;

selecting a specified number of profile library instances closest to the measured diffracted spectrum, the profile library instances including diffracted spectra and profile parameters, the profile parameters characterizing the profile of the integrated circuit structure, the profile library instances created with a specified extent of non-linearity;

deriving an adjustment multiplier, the adjustment multiplier configured to convert diffracted spectra of the selected number of profile library instances to corresponding profile parameters; and calculating refined profile parameters by multiplying the measured diffracted spectrum and the adjustment multiplier.

50. A method of determining the profile of an integrated circuit structure from a measured diffracted spectrum, the method comprising:

measuring a diffracted spectrum off a structure with a metrology device, the measurement generating a measured diffracted spectrum;

selecting a best match of the measured diffracted spectrum in a profile library, the profile library having instances with a specified extent of non-linearity, the profile library instances including profile parameters and associated diffracted spectrum, the profile parameters characterizing the profile of the integrated circuit structure, the best match being an instance of the profile library with diffracted spectrum closest to the measured diffracted spectrum;

selecting a specified number of profile library instances closest to the best match spectrum;

deriving an adjustment multiplier, the adjustment multiplier configured to convert diffracted spectra of the selected number of profile library instances to corresponding profile parameters; and calculating refined profile-parameters by multiplying the measured diffracted spectrum and the adjustment multiplier.

51. A method of adjusting the parameters of profile refinement for use in determining the profile of an integrated circuit structure, the method comprising:

measuring a diffracted spectrum off a structure with a metrology device, the measurement generating a measured diffracted spectrum;

determining refined profile parameters corresponding to the measured diffracted spectrum by using a refinement procedure and a profile library created at a specified resolution, the profile library having instances, the instances having profile parameters and associated diffracted spectra, the profile parameters characterizing the profile of the integrated circuit structure, the refinement procedure being a series of steps designed to determine refined profile parameters using the measured diffracted spectrum, data associated with the best match diffracted spectrum, and other data from and/or derived from the profile library;

deriving a multiplier for converting the profile parameters to a corresponding calculated diffracted spectrum, the derivation using data associated with selected instances of the profile library;

calculating a diffracted spectrum using the multiplier and the refined profile parameters of the measured diffracted spectrum; and comparing the goodness of fit of the calculated diffracted spectrum relative to the measured diffracted spectrum versus the goodness of fit of a best match diffracted spectrum from the profile library relative to the measured diffracted spectrum, the best match diffracted spectrum obtained by comparing the measured diffracted spectrum to diffracted spectra associated with instances of the profile library and selecting a diffracted spectrum closest to the measured diffracted spectrum.

52. The method of claim 51 wherein the goodness of fit comparison is performed by comparing the cost function of the calculated diffracted spectrum relative to the measured diffracted spectrum versus the cost function of the best match diffracted spectrum relative to the measured diffracted spectrum.

53. The method of claim 51 further comprising:
implementing a corrective action to improve the goodness of fit of the calculated diffracted spectrum relative to the measured diffracted spectrum.

54. The method of claim 53 wherein implementing the corrective action comprises recreating the profile library at a higher resolution than the original resolution.

55. The method of claim 53 wherein the implementing the corrective action comprises changing the refinement procedure to a different refinement procedure.

56. A method of determining the profile of an integrated circuit structure from a measured diffracted spectrum, the method comprising:
measuring a diffracted spectrum off a structure with a metrology device, the measurement generating a measured diffracted spectrum;
selecting a best match of the measured diffracted spectrum in a profile library, the profile library having instances with a specified extent of non-linearity, the profile library instances including profile parameters and associated diffracted spectrum, the profile parameters characterizing the profile of the integrated circuit structure, the best match being an instance of the profile library with diffracted spectrum closest to the measured diffracted spectrum;
selecting a first data point within a subset of the data space, the data space subset containing the profile parameters of the best match diffracted spectrum and profile parameters proximate to profile parameters of the best match diffracted spectrum;
simulating a diffracted spectrum off a structure with profile parameters corresponding the selected first data point;
verifying that a profile refinement preset criteria is met, the profile refinement preset criteria comprising a measure of goodness of fit of the simulated diffracted spectrum relative to the measured diffracted spectrum; and
extracting profile parameters associated with the simulated diffracted spectrum that meet the refinement preset criteria.

57. The method of claim 56 wherein verifying that the profile refinement preset criteria is met comprises:
testing if an error metric is within the profile refinement preset criteria, the error metric measuring the goodness of fit of the simulated diffracted spectrum relative to the measured spectrum; and
if the error metric is outside of the profile refinement preset criteria, performing an optimization technique to select the next data point within the data space subset, the next data point used to determine the next simulated diffracted spectrum.

58. The method of claim 57 wherein performing an optimization technique to select the next data point within the data space subset involves applying a global optimization technique and/or a local optimization technique.

59. The method of claim 56 wherein the data space is populated with data points generated by an optical metrology simulation process, the optical metrology simulation process calculating diffracted spectra off structures from a set of profile parameters at a specified resolution.

60. A method of determining the profile of an integrated circuit structure from a measured diffracted spectrum, the method comprising:
measuring a diffracted spectrum off a structure with a metrology device, the measurement generating a measured diffracted spectrum;
selecting a best match of the measured diffracted spectrum in a profile library, the profile library having instances with a specified extent of non-linearity, the profile library instances including profile parameters and associated diffracted spectrum, the profile parameters characterizing the profile of the integrated circuit structure, the best match being an instance of the profile library with diffracted spectrum closest to the measured diffracted spectrum;
calculating a sensitivity matrix, the sensitivity matrix being a measure of the change of the diffracted spectrum induced by a change of the profile parameters;
determining a first set of refined profile parameters using the calculated sensitivity matrix and the best match profile parameters;
simulating a first diffracted spectrum using the first set of refined profile parameters; and
determining a second set of refined profile parameters using the calculated sensitivity matrix and the first set of refined profile parameters.

61. The method of claim 60 further comprising:
simulating a second diffracted spectrum using the second set of refined profile parameters; and
determining a third set of refined profile parameters using the calculated sensitivity matrix and the second set of refined profile parameters.

62. A method of determining the profile of an integrated circuit structure from a measured diffracted spectrum, the method comprising:
measuring a diffracted spectrum off a structure with a metrology device, the measurement generating a measured diffracted spectrum;
selecting a best match of the measured diffracted spectrum in a profile library, the profile library having instances with a specified extent of non-linearity, the profile library instances including profile parameters and associated diffracted spectrum, the profile parameters characterizing the profile of the integrated circuit structure, the best match being an instance of the profile library with diffracted spectrum closest to the measured diffracted spectrum;
determining a first set of refined profile parameters using a refinement procedure, the refinement procedure being a series of steps designed to determine refined profile parameters using the measured diffracted spectrum, data associated with the best match diffracted spectrum, and other data from and/or derived from the profile library;
establishing ranges of the profile parameters around the first set of refined profile parameters;
creating a second profile library using the ranges established around the first set of refined profile parameters; and
determining a second set of refined profile parameters using a refinement procedure.

63. A system for determining the profile of an integrated circuit structure from a measured signal, the system comprising:
a profile query device configured to transmit a measured signal and to receive refined profile parameters, the measured signal obtained from an integrated circuit structure, the profile parameters characterize a possible profile of the integrated circuit structure;
a profile data space having data points with a specified extent of non-linearity, the data points representing profile parameters and associated signals; and a profile evaluator configured to select a best match of the measured signal in the profile data space, the best match being a data point of the profile data space with a signal closest to the measured signal, and configured to perform a refinement procedure to determine the refined profile parameters;

wherein the refinement procedure comprises a series of steps designed to determine refined profile parameters using the measured signal, data associated with the best match signal, and other data from and/or derived from the profile data space.

64. The system of claim 63 wherein the profile evaluator is configured to select a polyhedron in the profile data space, the polyhedron containing the best match data point and having corners corresponding to selected profile parameter data points proximate to the best match data point; and wherein the profile evaluator is configured to minimize a total cost function, the total cost function comprising a cost function of the signals corresponding to the selected profile parameter data points relative to the measured signal and a cost function of the best match signal relative to the measured signal.

65. The system of claim 63 wherein the profile evaluator is configured to compute a sensitivity matrix, the sensitivity matrix being a measure of the change of the signal induced by a change of the profile parameters;

wherein the profile evaluator is configured to determine an adjustment value of the profile parameters using the computed sensitivity matrix; and wherein the profile evaluator is configured to calculate the refined profile parameters by adding the adjustment value of the profile parameters to corresponding profile parameters of the best match data point in the profile data space.

66. The system of claim 63 wherein the profile evaluator is configured to select a best match of a measured signal by comparing the measured signal to signals of cluster representatives, the cluster representatives selected from clusters of data points of a profile data space, the data points of the profile data space having a specified extent of non-linearity, the data points representing profile parameters and associated signals, the profile parameters characterizing the profile of the integrated circuit structure; and wherein the profile evaluator is configured to calculate refined profile parameters by multiplying the measured signal and an adjustment multiplier matrix, the adjustment multiplier matrix converting the signal to profile parameters.

67. The system of claim 63 wherein the profile evaluator is configured to select a specified number of data points of a data space closest to a measured signal, the data points of the data space representing profile parameters and associated signals of a data space, the profile parameters characterizing the profile of the integrated circuit structure, the data points of the data space having a specified extent of non-linearity;

wherein the profile evaluator is configured to derive an adjustment multiplier, the adjustment multiplier converting signals associated with the selected number of data points to corresponding profile parameters; and wherein the profile evaluator is configured to calculate refined profile parameters corresponding to the measured signal by multiplying the measured signal and the adjustment multiplier.

68. The system of claim 63 wherein the profile evaluator is configured to select a best match of a measured signal in a profile data space, the data points representing profile parameters and associated signals, the profile parameters characterizing the profile of the integrated circuit structure, the best match being a data point of the profile data space with a signal closest to the measured signal;

wherein the profile evaluator is configured to select a first data point within a subset of the profile data space, the profile data space subset containing the measured signal and data points proximate to the data point associated with the best match signal;

wherein the profile evaluator is configured to simulate a signal off a structure with profile parameters corresponding the selected first data point;

wherein the profile evaluator is configured to ensure that a profile refinement preset criteria is met, the profile refinement preset criteria comprising a measure of goodness of fit of the simulated signal relative to the measured signal; and wherein the profile evaluator is configured to extract profile parameters associated with the simulated signal that meet the profile refinement preset criteria.

69. The system of claim 63 wherein the profile evaluator is configured to select a best match of a measured signal in a profile data space, the data points representing profile parameters and associated signals, the profile parameters characterizing the profile of the integrated circuit structure, the best match being a data point of the profile data space with a signal closest to the measured signal;

wherein the profile evaluator is configured to calculate a sensitivity matrix, the sensitivity matrix being a measure of the change of the signal induced by a change of the profile parameters;

wherein the profile evaluator is configured to determine a first set of refined profile parameters using the calculated sensitivity matrix and the best match profile parameters;

wherein the profile evaluator is configured to simulate a first signal using the first set of refined profile parameters; and wherein the profile evaluator is configured to determine a second set of refined profile parameters using the calculated sensitivity matrix and the first set of refined profile parameters.

70. The system of claim 63 wherein the profile evaluator is configured to select a best match of a measured signal in a profile data space, the data points representing profile parameters and associated signals, the profile parameters characterizing the profile of the integrated circuit structure, the best match being a data point of the profile data space with a signal closest to the measured signal;

wherein the profile evaluator is configured to determine a first set of refined profile parameters using a refinement procedure, the refinement procedure being a series of steps designed to determine refined profile parameters using the measured signal, data associated with the best match signal, and other data from and/or derived from the profile data space;

wherein the profile evaluator is configured to establish ranges of the profile parameters around the first set of refined profile parameters;

wherein the profile evaluator is configured to create a second profile data space using the ranges established around the first set of refined profile parameters; and wherein the profile evaluator is configured to determine a second set of refined profile parameters using the refinement procedure.

71. The system of claim 63 wherein the profile evaluator is configured to execute a refinement procedure that utilizes bilinear interpolation, Lagrange interpolation, Cubic Spline interpolation, Aitken interpolation, weighted average interpolation, multi-quadratic interpolation, bi-cubic interpolation, Turran interpolation, wavelet interpolation, Bessel's interpolation, Everett interpolation, finite-difference interpolation, Gauss interpolation, Hermite interpolation, Newton's divided difference interpolation, osculating interpolation, or Thiele's interpolation algorithm.

72. A system for determining the profile of an integrated circuit structure from a measured signal utilizing multiple refinement engines, the system comprising:

a profile query device configured to transmit a measured signal and to receive refined parameters, the measured signal obtained from an integrated circuit structure, the profile parameters characterize a possible profile of the integrated circuit structure;

a profile data space configured to store data points having profile parameters and associated signals; and a profile evaluator configured to invoke more than one refinement procedures to determine more than one set of refined profile parameters, configured to select a best match signal, the best match being a data point of the profile data space with a signal closest to the measured signal, configured to select a set of refined profile parameters from the more than one set of refined profile parameters based on a specified selection criteria;

wherein the refinement procedure comprises a series of steps designed to determine refined profile parameters using the measured signal, data associated with the best match signal, and other data from and/or derived from the profile data space.

73. A system for determining the profile of an integrated circuit structure from a measured signal generated by a metrology device, the system comprising:

a metrology device configured to measure a signal off an integrated circuit structure and to transmit the measured signal, the measured signal obtained from an integrated circuit structure, the profile parameters characterize a possible profile of the integrated circuit structure;

a profile query device configured to transmit a query for profile parameters and to receive refined profile parameters;

a profile data space configured to store data points, the data points having signals and associated profile parameters; and a profile evaluator configured to select a best match of the measured signal in the profile data space, the best match being a data point of the profile data space with a signal closest to the measured signal, configured to invoke one or more refinement procedures to determine one or more sets of refined profile parameters, configured to select a set of refined profile parameters from the one or more sets of refined profile parameters based on a specified selection criteria, and configured to transmit the refined profile parameters to the profile query device;

wherein the refinement procedure comprises a series of steps designed to determine refined profile parameters using the measured signal, data associated with the best match signal, and other data from and/or derived from the profile data space.

74. The system of claim 73 wherein the metrology device is an optical metrology device, an electron metrology device, an electric metrology device, or a mechanical metrology device.

75. A computer-readable storage medium containing computer executable code to determine the profile of an integrated circuit structure from a measured signal by instructing a computer to operate as follows:

selecting a best match of a measured signal in a profile data space, the measured signal obtained from an integrated circuit structure, the profile data space having data points with a specified extent of non-linearity, the data points representing profile parameters and associated signals, the profile parameters characterizing the profile of the integrated circuit structure, the best match being a data point of the profile data space with a signal closest to the measured signal; and performing a refinement procedure to determine refined profile parameters corresponding to the measured signal;

wherein the refinement procedure comprises a series of steps designed to determine refined profile parameters using the measured signal, data associated with the best match signal, and other data from and/or derived from the profile data space.

76. A computer-readable storage medium containing computer executable code to determine the profile of an integrated circuit structure from a measured signal by instructing a computer to operate as follows:

selecting a best match of a measured diffracted spectrum in a profile library, the measured spectrum obtained from an integrated circuit structure, the profile library having instances with a specified extent of non-linearity, the profile library instances including profile parameters and associated diffracted spectrum, the profile parameters characterizing the profile of the integrated circuit structure, the best match being an instance of the profile library with diffracted spectrum closest to the measured diffracted spectrum; and performing a refinement procedure to determine refined profile parameters corresponding to the measured spectrum;

wherein the refinement procedure comprises a series of steps designed to determine refined profile parameters using the measured signal, data associated with the best match signal, and other data from and/or derived from the profile data space.

* * * * *